United States Patent
Beck et al.

(10) Patent No.: US 12,318,818 B2
(45) Date of Patent: Jun. 3, 2025

(54) CLEANING UNIT AND A MEDICAL IMAGING APPARATUS WITH A CLEANING UNIT

(71) Applicant: Siemens Healthineers AG, Forchheim (DE)

(72) Inventors: Thomas Beck, Dormitz (DE); Florian Meise, Hausen (DE); Stefanie Gügel-Wild, Langensendelbach (DE); Tobias Kotulla, Stuttgart (DE); Martin Seifert, Bayreuth (DE)

(73) Assignee: Siemens Healthineers AG, Forchheim (DE)

( * ) Notice: Subject to any disclaimer, the term of this patent is extended or adjusted under 35 U.S.C. 154(b) by 201 days.

(21) Appl. No.: 17/947,493

(22) Filed: Sep. 19, 2022

(65) Prior Publication Data
US 2023/0090506 A1    Mar. 23, 2023

(30) Foreign Application Priority Data
Sep. 21, 2021    (DE) .......................... 102021210471.1

(51) Int. Cl.
*B08B 1/30*     (2024.01)
*A61B 5/055*    (2006.01)
*A61L 2/10*     (2006.01)
*B08B 1/14*     (2024.01)
*B08B 1/16*     (2024.01)
*B08B 13/00*    (2006.01)

(52) U.S. Cl.
CPC ............... *B08B 1/30* (2024.01); *A61L 2/10* (2013.01); *B08B 1/143* (2024.01); *B08B 1/165* (2024.01); *B08B 13/00* (2013.01); *A61B 5/055* (2013.01); *A61L 2202/17* (2013.01); *A61L 2202/24* (2013.01)

(58) Field of Classification Search
CPC ......... A61B 6/00; A61B 6/4423; A61B 6/035; A61L 2/0047; A61L 2/0088
See application file for complete search history.

(56) References Cited

U.S. PATENT DOCUMENTS

| 5,918,342 A | 7/1999 | Smith et al. |
| 2023/0136855 A1* | 5/2023 | Nagel ................... A61L 2/0047 422/22 |

FOREIGN PATENT DOCUMENTS

| CN | 203524686 U | * 4/2014 | |
| DE | 102020207984 A1 | * 12/2021 | ............. A61B 6/035 |

OTHER PUBLICATIONS

UPenn, "Device for MRI scanner intra-bore disinfection"; https://upenn.technologypublisher.com/technology/40453 Stand: Jun. 23, 2020.
(Continued)

*Primary Examiner* — Shay Karls
(74) *Attorney, Agent, or Firm* — Banner & Witcoff Ltd.

(57) ABSTRACT

A cleaning unit for cleaning a housing of a medical imaging apparatus surrounding a patient receiving area, including at least one cleaning element, wherein the at least one cleaning element has an annular carrier structure, and a diameter of the cleaning element comprises at least one value of a diameter of the housing surrounding the patient receiving area.

20 Claims, 14 Drawing Sheets

(56) References Cited

OTHER PUBLICATIONS

"ISO 17664:2017—Processing of health care products—Information to be provided by the medical device manufacturer for the processing of medial devices", ISO, https://www.iso.org/standard/62952.html, abgerufen am Apr. 24, 2020.

"MRI Non-Magnetic MagnaWand Cleaning Wand", mriequip.com/store/pc/MRI-Non-Magnetic-Magna-Wand-Cleaning-Wand-p383.htm (Stand: Mar. 18, 2021).

Ledsmagazine: "PDC develops UV-C-enabled disinfection system for medical radiology bores and tables (Updated)";Year: Nov. 5, 2020; URL: https://www.ledsmagazine.com/lightinghealthwellbeing/article/14186807/pdcdevelopsuvcenabled-disinfection-system-for-medical-radiology-bores-and-tables.

auntminnieeurope.com.: "MRI cleaning kit gets tested in Melbourne"; Year: Nov. 25, 2020; URL:https://www.auntminnieeurope.com/index.aspxsec=ser&sub-def&pag=dis&ItemID=619549.

\* cited by examiner

CLEANING UNIT AND A MEDICAL IMAGING APPARATUS WITH A CLEANING UNIT

TECHNICAL FIELD

The present disclosure relates to a cleaning unit, which is embodied for cleaning a housing of a medical imaging apparatus surrounding a patient receiving area, comprising at least one cleaning element. The present disclosure moreover relates to a medical imaging apparatus with a scanner unit, a patient receiving area at least partly surrounded by the scanner unit, a housing surrounding the patient receiving area and a cleaning unit.

BACKGROUND

In medical imaging apparatuses with a cylindrical and/or tubular patient receiving area, the patient is positioned within the patient receiving area for a medical imaging examination. The patient receiving area is surrounded in this case by a scanner unit and/or a detector unit of the medical imaging apparatus, wherein the patient is positioned on a patient table and moved into the patient receiving area for a medical imaging examination. After a medical imaging examination it is necessary and/or desirable to clean the housing of the patient receiving area surrounding the patient receiving area.

In particular when the medical imaging apparatus is embodied as a magnetic resonance apparatus, the patient receiving area is embodied very long and tunnel-shaped and thus has a length of 1.5 m or more. PET apparatuses (Positron-Emission-Tomography apparatuses) and/or PET computed tomography apparatuses and/or PET magnetic resonance apparatuses also have a similarly long and/or large patient receiving area. Cleaning a patient receiving area embodied in this way is however only possible with a significant outlay in labor for a medical operator and/or cleaning personnel. Moreover cleaning a patient receiving area embodied in this way is very time-consuming.

While the patient is present within the patient receiving area, individual areas can be contaminated by the patient, such as for example by them touching and/or breathing on these areas. Therefore an irradiation of the patient receiving area and/or of a housing surrounding a patient receiving area with UV radiation, in particular with UV-C radiation, is not sufficient for an efficient cleaning. Instead it is necessary for cleaning personnel to be moved into the patient receiving area with the patient table and to carry out a manual wipe disinfection of the housing surrounding the patient receiving area there. Furthermore a sponge mounted on a telescopic arm can also be introduced by cleaning personnel into the patient receiving area for cleaning, as is disclosed in U.S. Pat. No. 5,918,342 A.

These types of cleaning methods are very laborious and time-consuming however. Moreover there is the danger that, because of time pressure, the cleaning will only be carried out inadequately.

SUMMARY

An underlying object of the present disclosure is in particular to provide cleaning for a housing of a medical imaging apparatus surrounding a patient receiving area that is simple to carry out and efficient. The object is achieved by the features of the independent claims. Advantageous aspects are described in the dependent claims.

The disclosure is based on a cleaning unit that is embodied for cleaning a housing of a medical imaging apparatus surrounding a patient receiving area, comprising at least one cleaning element. In accordance with the disclosure the at least one cleaning element has an annular carrier structure, wherein a diameter of the cleaning element comprises at least one value of a diameter of the housing surrounding the patient receiving area.

The cleaning unit is embodied for cleaning, preferably automatic cleaning, of the patient receiving area, in particular of the housing of a medical imaging apparatus surrounding the patient receiving area. To this end the cleaning unit has at least one cleaning element with an annular carrier structure. Preferably a circumference and/or a geometry of the cleaning element, in particular of the annular carrier structure, is adapted to a circumference and/or a geometry, in particular a cross section, of the patient receiving area and/or of the housing surrounding the patient receiving area. Preferably the cleaning element with the annular carrier structure is embodied for cleaning of the patient receiving area, in particular of the housing surrounding the patient receiving area. Here the annular carrier structure can rest in a movable manner against the housing surrounding the patient receiving area, so that by way of a movement of the cleaning element, in particular of the annular carrier structure, in the longitudinal direction of the patient receiving area, a wiping over the housing surrounding the patient receiving area can take place.

Especially advantageously here the cleaning element with the annular carrier structure rests in the circumferential direction of the patient receiving area against the housing surrounding the patient receiving area. The annular carrier structure in this case can comprise a contact surface on a side facing toward the housing surrounding the patient receiving area, which is arranged in the circumferential direction around the annular carrier structure. Preferably in this case the contact surface in the circumferential direction can extend around the entire area of the annular carrier structure facing toward the housing surrounding the patient receiving area.

If the diameter, in particular the outer diameter, of the at least one cleaning element corresponds to the diameter of the housing surrounding the patient receiving area, in particular an inner diameter of the housing surrounding the patient receiving area, then a tight-fitting introduction of the cleaning unit, in particular of the at least one cleaning element with the annular carrier structure, into the patient receiving area is possible. For a cleaning of the patient receiving area, in particular of the housing surrounding the patient receiving area it is necessary for the at least one cleaning element to rest against the patient receiving area with a sufficiently large force to enable the wipe disinfection to be carried out. Preferably here the at least one cleaning element rests against the housing surrounding the patient receiving area with a force of 4 N to 6 N. Especially advantageously the at least one cleaning element rests against the housing surrounding the patient receiving area with a force of approx. 5 N, so that sufficiently large pressure for a mechanical cleaning is present, but also a movement of the cleaning unit through the patient receiving area, in particular in the longitudinal direction of the patient receiving area, is possible. To this end the diameter, in particular the outer diameter, of the at least one cleaning element can also be approx. 1 mm greater than the diameter, in particular the inner diameter, of the housing surrounding the patient receiving area. In particular here the diameter, in particular the outer diameter, of the at least one cleaning element can be approx. 2 mm greater than the diameter, in particular the inner diameter, of the housing surrounding the patient receiving area. In particular here the diameter, in particular the outer diameter, of the at least one cleaning element can be a maximum of 3 mm greater than the diameter, in particular the inner diameter, of the housing surrounding the patient receiving area.

Moreover the at least one cleaning element can additionally have a cleaning surface, for example a wiping lip and/or a textile fabric, such as a cleaning fleece. A cleaning surface of this type can be arranged on a contact surface of the at least one cleaning element, in particular of the annular carrier element. A cleaning surface of this type has a thickness that can be sufficient for the annular carrier structure with a diameter, which corresponds to the circumference, in particular the inner circumference, of the housing surrounding the patient receiving area, to rest with a sufficiently great force against the housing surrounding the patient receiving area. Depending on an aspect of the cleaning surface, in particular a thickness of the cleaning surface, the annular carrier structure of the at least one cleaning element can also have a diameter that is greater or also less than a value of the diameter of the patient receiving area, so that the annular carrier structure always rests with a force great enough for the cleaning of the patient receiving area against the housing surrounding the patient receiving area. If the at least one cleaning element does not have a cleaning surface, then preferably a diameter, in particular an outer diameter, of the annular carrier structure corresponds to the diameter, in particular the outer diameter, of the at least one cleaning element.

The disclosure advantageously enables simple and time-saving cleaning of the housing surrounding the patient receiving area to be provided for medical operating personnel. In particular in this way a cleaning workflow with reduced labor outlay for cleaning the housing surrounding the patient receiving area can be made available for medical operating personnel and/or cleaning personnel. In this case the at least one cleaning element with the annular carrier structure enables a large coverage, preferably a complete coverage, in the circumferential direction of the patient receiving area to be achieved for a cleaning of the housing surrounding the patient receiving area. In particular, by way of movement of the cleaning element with the annular carrier structure within the patient receiving area, in particular in the longitudinal direction of the patient receiving area, a simple full-coverage cleaning, in particular a mechanical wiping, of the housing surrounding the patient receiving area can be made possible.

In an advantageous development of the inventive cleaning unit it is proposed that the at least one cleaning element has at least one base element, which is embodied for an arrangement of the annular carrier structure within the patient receiving area. Preferably the at least one base element is embodied for a movable arrangement within the patient receiving area. In this case the at least one base element can be embodied for an arrangement on a rail system of the medical imaging apparatus and/or for an arrangement on a patient support apparatus, in particular a patient table of the patient support apparatus. To this end the at least one base element can also comprise at least one attachment element for a secure arrangement of the cleaning unit on a rail system of the medical imaging apparatus and/or on the patient support apparatus, in particular the patient table of the patient support apparatus. By means of the base element a high stability of the cleaning unit, in particular of the annular carrier structure, during a cleaning process, in particular a movement of the cleaning unit within the patient receiving area, for cleaning of the housing surrounding the patient receiving area can be achieved.

In an advantageous development of the inventive cleaning unit it is proposed that the annular carrier structure has at least two ring elements, wherein the two ring elements are each arranged at a first end area on the at least one base element and at least partly in a movable manner in relation to one another with a second end area facing away from the at least one base element. The annular carrier structure can in this case have a common base element on which the two ring elements can preferably be arranged on opposite sides. Moreover the annular carrier structure can also comprise two base elements, wherein one of the two ring elements in each case can be arranged on one of the two base elements. Preferably the at least two ring elements are arranged in an annular shape. In this case the two ring elements can also be arranged essentially mirror-symmetrically in relation to one another.

The second end areas of the two ring elements, facing away from the at least one base element, can in this case be embodied resting against one another and/or at least partly overlapping. If the cleaning unit and thus also the annular carrier structure is located outside of the patient receiving area, the two ring elements are preferably in a relaxed state. In this relaxed state a diameter, in particular an outer diameter, of the at least one cleaning element has at least the same value or a greater value than a diameter, in particular inner diameter, of the housing surrounding the patient receiving area. For example the diameter, in particular an outer diameter, of the at least one cleaning element can be embodied greater by max. 1 mm, preferably by max. 2 mm and preferably by max. 3 mm than the diameter, in particular inner diameter, of the housing surrounding the patient receiving area. If on the other hand the cleaning unit and thus also the at least one cleaning element with the annular carrier structure is moved into the patient receiving area, then the annular carrier structure can be pressed together by a funnel-shaped aspect of an introduction area of the patient receiving area during its introduction into the patient receiving area. This enables the two ring elements to be moved toward one another and/or to be pressed inward, so that an overlap area between the two ring elements can also be enlarged. The effect of this is that the two ring elements are put under tension and thus exert a force on the housing surrounding the patient receiving area.

This aspect has the advantage that a force acting on the housing surrounding the patient receiving area can be created in a constructively simple way for cleaning, in particular mechanical cleaning, of the housing surrounding the patient receiving area.

As an alternative to this the cleaning unit, in particular the annular carrier structure, can also comprise a spring element, which pushes the two ring elements outward for a cleaning process.

In an advantageous development of the inventive cleaning unit it is proposed that the at least one cleaning element has at least one cleaning covering, wherein cleaning covering is arranged on the annular carrier structure. Preferably the at least one cleaning covering is arranged on the annular carrier structure on an outer side of the annular carrier structure. For example, for this purpose the annular carrier structure can have a contact surface, which is embodied to accept and/or fasten the at least one cleaning covering to this outer side. Moreover the contact surface can also be provided with an attachment element, which makes possible a simple-to-release attachment of the at least one cleaning covering to the annular carrier structure, so that the cleaning covering is able to be replaced. For example the attachment element can have a hook and loop fastening. In particular here the at least one cleaning covering is arranged in the circumferential direction of the annular carrier structure over an entire length of the annular carrier structure. Moreover further arrangement variants of the at least one cleaning covering on the annular carrier structure appearing sensible to the person skilled in the art are always conceivable.

The at least one cleaning covering can in this case comprise a material that is suitable and/or embodied for accepting a cleaning fluid. Preferably the at least one cleaning covering comprises a foam and/or flexible shaped textile, such as for example a non-woven material. As an alternative to this the at least one cleaning covering can also comprise a wiping lip and/or a cleaning lip, preferably made from an elastic material. Moreover further aspects of the at least one cleaning covering appearing sensible to the person skilled in the art are always conceivable.

This aspect of the disclosure makes possible an efficient cleaning of the housing surrounding the patient receiving area. In particular in this way a mechanical cleaning, in particular a wiping, of the surface of the housing is made possible.

In an advantageous development of the inventive cleaning unit it is proposed that the cleaning unit has at least one receiving element for receiving a cleaning agent. The cleaning agent preferably comprises a disinfection agent, in particular a disinfection agent approved for medical imaging apparatuses. The at least one receiving element can for example comprise a mounting for receiving a commercially available cleaning agent holder with cleaning agent. In particular the at least one receiving element can be embodied in such a way that it is possible to exchange a cleaning agent container and/or a disinfection agent container at any time. Moreover the cleaning unit can also have more than one receiving element for receiving a cleaning agent. If for example the annular carrier structure comprises two ring elements, then the cleaning unit can also have two receiving elements for receiving a cleaning agent, wherein one of the two receiving elements is arranged on one of the two ring elements in each case. This enables short transmission paths for a cleaning agent from the at least one receiving element to be provided to a cleaning covering of the cleaning unit for example.

In an advantageous development of the inventive cleaning unit it is proposed that the at least one receiving element is arranged on an inner side of the annular carrier structure. The inner side of the annular carrier structure can for example comprise a side of the annular carrier structure facing away from a cleaning covering and/or a side of the annular carrier structure facing away from the housing surrounding the patient receiving area. This aspect of the disclosure makes possible an especially protected arrangement of the at least one receiving element and/or of the cleaning agent. In particular with a movement of the cleaning unit through the patient receiving this advantageously enables unwanted damage to the at least one receiving element to be prevented.

In an advantageous development of the inventive cleaning unit it is proposed that the at least one cleaning element has at least one cleaning agent channel, which is arranged at least partly running around within the annular carrier structure. The annular carrier structure in this case can comprise a groove to receive the at least one cleaning agent channel. The at least one cleaning agent channel can moreover comprise a tube or also be embodied as a kind of tube.

Preferably here the at least one cleaning agent channel can have openings at defined and/or specific distances, through which the cleaning agent can escape, in particular to a cleaning agent surface and/or to the housing surrounding the patient receiving area. If the annular carrier structure has a plurality of ring elements, then the at least one cleaning element can also comprise a plurality of cleaning agent channels, wherein one cleaning agent channel can be arranged in each case in one of the ring elements of the annular carrier. This aspect of the disclosure has the advantage that a simple and rapid distribution of the cleaning agent can be provided. In particular in this way an even distribution of the cleaning agent to the annular carrier structure, in particular to a cleaning covering of the annular carrier structure, can be achieved.

In a preferred development the at least one cleaning agent channel can also be connected to the receiving element for receiving a cleaning agent, so that a simple distribution of the cleaning agent can be achieved. In this case for example, a cleaning agent is distributed by manual operation of a cleaning agent dispenser, which is comprised by a receiving element for receiving a cleaning agent. Moreover an automatic control of the cleaning agent distribution is also conceivable.

In an advantageous development of the inventive cleaning unit it is proposed that the at least one cleaning element has a sensor for detecting an amount of cleaning agent. The sensor can preferably be embodied in such a way that the amount of cleaning agent is able to be detected with the aid of a moisture value and/or a moisture content. Preferably the sensor detects the moisture value and/or the moisture content within the cleaning covering and/or in a vicinity of the cleaning covering. To do this the sensor can be arranged directly in the cleaning covering. Moreover it is also conceivable for the sensor to be arranged in a contact surface on the support of the cleaning covering and thus to be arranged in direct contact with the cleaning covering.

This aspect of the disclosure has the advantage that before a cleaning process an amount of cleaning agent present in the cleaning covering can be tested and/or checked by means of the cleaning unit. In particular in this way it is possible to prevent a cleaning process from being carried out with too little cleaning agent and therefore the cleaning being inadequate. Furthermore the cleaning process can be prevented from being carried out with too much cleaning agent. Moreover the sensor can be connected to an optical output element that displays to a user an amount of cleaning agent. For example the optical output element can comprise an LED, which shows a red light for too little cleaning agent or for too much cleaning agent.

In an advantageous development of the inventive cleaning unit it is proposed that the at least one cleaning element has a plurality of UV-C illumination means that are arranged on an outer surface of the annular carrier structure. The plurality of UV-C illumination means preferably comprise a large number of UV-C illumination means. The plurality of UV-C illumination means preferably comprise a plurality of UV-C LEDs, so that an especially low-cost cleaning unit can be provided. The UV-C illumination means, in particular the UV-C LEDs, can be arranged in this case at defined and/or specific distances apart, so that an effective surface disinfection of the housing surrounding the patient receiving area can be achieved. To this end the annular carrier structure can also have an annular recess, in which the UV-C illumination means, in particular the UV-C LEDs, are arranged, so that moreover a protected arrangement can be obtained during movement of the cleaning unit through the patient receiving area.

In an advantageous development of the inventive cleaning unit it is proposed that the at least one cleaning element has at least one illumination means and at least one light opening, wherein the light opening is arranged on an inner side and/or a side surface of the annular carrier structure. In this way a cleaning process can advantageously be displayed visually for a user and/or a patient. The at least one illumination means can for example comprise a UV-C illumination means, which can be used additionally for disinfection of the housing surrounding the patient receiving area. Moreover the at least one illumination means can also comprise an illumination means designed only for a visual display of a cleaning process, which only lights up during a cleaning process. For example the at least one illumination means comprises an LED here, which emits light with a blue color, which can create an impression of cleanliness for an observer. The at least one light opening makes it possible for the light emitted by the at least one illumination means to be visible for a user and/or a patient. The at least one light opening on the annular carrier structure can for example comprise a gap and/or channel, in which the at least one illumination means is also arranged.

In an advantageous development of the inventive cleaning unit it is proposed that the cleaning unit has an electrical connection element. By means of the electrical connection element of the cleaning unit, the cleaning unit can be supplied with electrical energy and/or an exchange of data with a control unit, for example a control unit of the medical imaging apparatus, is possible. In this case the electrical connection element can be connected directly to a control unit and/or to an electrical contact. Preferably the electrical connection element here is connected via a plug connection to a patient support apparatus, in particular to a patient table of the patient support apparatus, of the medical imaging apparatus to a control unit and/or to an electrical contact.

This aspect of the disclosure has the advantage that advantageously an automatic and/or autonomous control of the cleaning unit and thus of a cleaning process for cleaning the housing surrounding the patient receiving area can be provided. Furthermore a simple control of a cleaning, in particular of a cleaning process, can also be made possible as a function of a type of medical imaging examination. Further an advantageous automatic documentation of cleaning processes can be provided.

In an advantageous development of the inventive cleaning unit it is proposed that the electrical connection element of the cleaning unit is compatible with a socket of a patient table for electrical contacting of local radio frequency coils. Preferably the medical imaging apparatus here comprises a magnetic resonance apparatus, in which local radio frequency coils can be employed for acquisition of magnetic resonance signals. For the acquisition of magnetic resonance signals frequently at least one local radio frequency coil is positioned on the patient, in particular around the region of the patient to be examined, for a magnetic resonance examination. For different regions to be examined different local radio frequency coils are also available for an acquisition of magnetic resonance signals, wherein the different local radio frequency coils are each adapted to the region to be examined, such as for example a head radio frequency coil or a knee radio frequency coil etc. For an electrical contacting and/or an exchange of data of the local radio frequency coil, the local radio frequency coil has a coil plug connector. Moreover the patient support apparatus, in particular the patient table, of the magnetic resonance apparatus also has a corresponding and/or compatible coil connector element for this purpose, in particular a plug socket, so that electrical contact between the local radio frequency coil can take place directly at the patient table. This type of plug socket already present on the patient table can also be used for electrical contacting of the cleaning unit, wherein the electrical connection element of the cleaning unit can be constructed in this case in a similar way to a coil plug connector element. Through this a short cable length for the electrical connection element can be achieved and thus the danger of cables being squashed during a movement of the patient table can be minimized. Moreover in this way the cleaning unit can also be integrated especially easily into medical imaging apparatuses that already exist, in particular magnetic resonance apparatuses.

The disclosure is furthermore based on a medical imaging apparatus with a scanner unit, a patient receiving area at least partly surrounded by the scanner unit, a housing surrounding the patient receiving area and a cleaning unit. The cleaning unit in this case is embodied for cleaning the housing surrounding the patient receiving area of the medical imaging apparatus and comprises at least one cleaning element, which has an annular carrier structure, wherein a diameter of the cleaning element comprises at least one value of a diameter of the housing surrounding the patient receiving area.

The medical imaging apparatus in this case can for example comprise a magnetic resonance apparatus and/or computed tomography apparatus and/or a PET (Positron Emission Tomography) apparatus and/or further medical imaging apparatuses appearing sensible to the person skilled in the art. The medical imaging apparatus preferably comprises a detector unit and/or a scanner unit, which is embodied and/or designed for acquisition of medical image data during the medical imaging examination on the patient. If for example the medical imaging apparatus is embodied as a magnetic resonance apparatus, the scanner unit can comprise a basic magnet for creating a homogeneous magnetic field, a gradient system for a spatial encoding of the acquired magnetic resonance data and a radio frequency antenna unit. The radio frequency antenna unit in this case can comprise a radio frequency antenna arranged permanently within the scanner unit for emitting an excitation pulse.

For a medical imaging examination the patient, in particular the region of the patient to be examined, is positioned within the patient receiving area. A field of view (FOV) and/or an isocenter of the medical imaging apparatus are preferably arranged within the patient receiving area. The FOV preferably comprises an acquisition region of the medical imaging apparatus, within which the conditions for an acquisition of medical imaging data are present. The isocenter of the medical imaging apparatus preferably comprises the region and/or point within the medical imaging apparatus that has the optimal and/or ideal conditions for the acquisition of medical imaging data. For example in the aspect of the medical imaging apparatus as a magnetic resonance apparatus the isocenter is the most homogeneous magnetic field region within the magnetic resonance apparatus.

The housing surrounding the patient receiving area preferably surrounds the patient receiving area in a cylindrical shape. In this case the housing surrounding the patient receiving area can comprise a housing shell. In the event of the medical imaging apparatus being embodied as a magnetic resonance apparatus, the housing surrounding the patient receiving area can also be embodied as a single part and/or in one piece with the radio frequency antenna unit of the scanner unit.

The inventive medical imaging apparatus advantageously enables simple and time-saving cleaning of the housing surrounding the patient receiving area to be provided for a medical operator and/or cleaning personnel. In particular in this way a cleaning workflow with reduced outlay of labor for cleaning the housing surrounding the patient receiving area can be made available to a medical operator and/or cleaning personnel. In this case the at least one cleaning element with the annular carrier structure enables a large coverage, preferably a complete coverage, to be achieved in the circumferential direction of the patient receiving area for a cleaning of the housing surrounding the patient receiving area. In particular, by way of movement of the cleaning element with the annular carrier structure within the patient receiving area, in particular in the longitudinal direction of the patient receiving area, a simple full-coverage cleaning, in particular a mechanical wiping, of the housing surrounding the patient receiving area can be made possible.

The advantages of the inventive medical imaging apparatus essentially correspond to the advantages of the inventive cleaning unit, which have been set out in detail above. Features, advantages or alternate forms of aspect can likewise be transferred to the other claimed subject matter and vice versa.

In an advantageous development of the inventive medical imaging apparatus it is proposed that the annular carrier structure for cleaning of the housing surrounding the patient receiving area is arranged within the patient receiving area and rests with a force against the housing surrounding the patient receiving area.

The force with the annular carrier structure rests against the housing surrounding the patient receiving area can be brought about for example by a pre-tensioning of the annular carrier structure and/or by a spring element. Preferably the annular carrier structure rests against the housing surrounding the patient receiving area with a force of 4 N to 6 N. Especially advantageously the annular carrier structure rests against the housing surrounding the patient receiving area with a force of approx. 5 N.

This aspect has the advantage that a sufficiently high pressure of the at least one cleaning element can be provided for effective cleaning of the housing surrounding the patient receiving area, but at the same time a pressure acting on the housing of the patient receiving area is not so great that it would prevent a movement of the at least one cleaning element for a cleaning process within the patient receiving area.

In an advantageous development of the inventive medical imaging apparatus it is proposed that the medical imaging apparatus has a patient support apparatus with a patient table able to be moved within the patient receiving area, wherein the patient table has a receiving unit for an arrangement of the cleaning unit, wherein the receiving unit is arranged at a head end of the patient table.

The patient support apparatus is embodied for positioning the patient, in particular the region of the patient to be examined, within the patient receiving area, in particular within the isocenter of the medical imaging apparatus. For this purpose the patient support apparatus has the patient table. The patient table is embodied in particular for a horizontal movement within the patient receiving area. Moreover the patient table can also be embodied for a vertical movement. A vertical movement of the patient table is then only possible for example when the patient table is arranged completely outside the patient receiving area, so that it can be made possible more easily for the patient to sit up on the patient table. The patient, in particular the region of the patient to be examined, is introduced into the patient receiving area by means of the movable patient table, in particular into the isocenter of the medical imaging apparatus.

The head end of the patient table preferably comprises that end area of the patient table that moves into the patient receiving area first when the patient table is moved into the patient receiving area. In particular the head end of the patient table comprises a forward end area of the patient table. The receiving unit of the patient table preferably comprises specifically embodied areas and/or specifically embodied elements on the patient table, which are embodied for arranging and/or accommodating the cleaning unit on the patient table.

This aspect of the disclosure has the advantage that a simple cleaning movement of the cleaning unit, in particular of the at least one cleaning element, can be achieved by an arrangement of the cleaning unit on the patient table. In particular, through a horizontal movement of the patient table within the patient receiving area, the cleaning unit, in particular the at least one cleaning element with the annular carrier structure, can be moved for cleaning through the patient receiving area. A further advantage of this aspect of the disclosure is that a simple cleaning workflow can be made available for a user.

In an advantageous development of the inventive medical imaging apparatus it is proposed that the patient table has an attachment rail for attachment of at least one accessory unit, wherein the receiving unit comprises the attachment rail, and that the cleaning unit comprises at least one attachment element corresponding to the attachment rail. Accessory units can be required for medical imaging examinations, which are attached and/or arranged for example during a preparation of the medical imaging examination of the patient. Such an accessory unit can for example comprise an EKG unit and/or an infusion unit and/or further units appearing sensible to the person skilled in the art. Moreover the accessory unit can comprise a supporting unit, such as for example a support pillow, for correct and/or more comfortable support and/or positioning of the patient on the patient table. In the case of a magnetic resonance examination an accessory unit can also comprise a local radio frequency coil, which is arranged and/or positioned around a region of the patient to be examined during a preparation of the medical imaging examination. In order to arrange these accessory units securely, in particular in a fixed position, on the patient table, these are frequently secured by means of an attachment strap. These straps are arranged on the attachment rail. Preferably the patient table has two attachment rails, which are arranged in the longitudinal direction of the patient table on side areas of the patient table. In this case the attachment rails can be arranged at opposing side areas of the patient table, wherein a support area for support of the patient is preferably arranged between the two attachment rails.

The at least one attachment element of the cleaning unit embodied correspondingly to the attachment rail is preferably embodied, together with the attachment rail, to make possible an attachment and/or arrangement of the cleaning unit, in particular an attachment and/or arrangement of the cleaning unit that can be detached again, on the patient table.

This aspect of the disclosure has the advantage that a simple arrangement of the cleaning unit of the patient table can be achieved. In particular here with already existing medical imaging apparatuses a simple integration of the cleaning unit is made possible, without any constructional changes to the existing medical imaging apparatus, in particular to the patient table, being required here. Furthermore an especially space-saving and low-cost integration of the cleaning unit on the patient table can be realized.

In an advantageous development of the inventive medical imaging apparatus it is proposed that the medical imaging apparatus has a patient support apparatus with a patient table and a rail system arranged within the patient receiving area for a guidance of the patient table within the patient receiving area, wherein the cleaning unit is able to be arranged on the rail system for cleaning of housing surrounding the patient receiving area. Preferably the rail system runs in the longitudinal direction of the patient receiving area through the entire patient receiving area. The rail system in this case typically comprises two rails, which run and/or are arranged on both sides in side areas of the patient receiving area.

An arrangement of the cleaning unit on the rail system advantageously enables a simple and secure guidance of the cleaning unit during a movement through the patient receiving area, in particular in the longitudinal direction through the patient receiving area to be achieved. In particular in this case a simple integration of the cleaning unit is made possible with already existing medical imaging apparatuses, without any constructional changes to the existing medical imaging apparatus being required here. A further advantage is that, with an additional coupling of the cleaning unit to the patient table, the load on a coupling mechanism between the cleaning unit and the patient table can advantageously be relieved.

Moreover, through the arrangement of the cleaning unit on the rail system of the medical imaging apparatus, the cleaning unit can be moved manually through the patient receiving area, for example by means of a telescopic rod, for cleaning and thus a simple and low-cost cleaning unit can be provided.

In an advantageous development of the inventive medical imaging apparatus it is proposed that the cleaning unit has at least one attachment element and the receiving unit, on an end face side of the patient table, has at least one attachment element corresponding to the at least one attachment element of the cleaning unit. In this way a simple and in particular autonomous arrangement and/or attachment of the cleaning unit to the patient table can be achieved. If moreover the cleaning unit is arranged on the rail system, during an inward movement of the patient table the cleaning unit can be coupled and/or attached to the patient table and moved for a cleaning through the patient receiving area.

In this case the at least one attachment element of the cleaning unit can comprise a web-shaped attachment element extending away from the cleaning unit in the direction of the patient table. Preferably the at least one attachment element of the receiving unit comprises a corresponding hole-shaped receiving element.

In an advantageous development of the inventive medical imaging apparatus it is proposed that an attachment mechanism of the cleaning unit and the patient table is embodied in such a way that, when the patient table exits from the patient receiving area, the attachment mechanism is released. Preferably the attachment mechanism is embodied in such a way, that, when the patient table is moved into the patient receiving area, the patient table with the cleaning unit connects an attachment and/or coupling. An advantage of this aspect is that the cleaning unit can remain protected within the patient receiving area. Moreover in this way the cleaning unit remains arranged outside the field of view of a patient positioned on the patient table, so that the cleaning unit can be arranged on the end face side of the patient table even during a medical imaging examination.

In an advantageous development of the inventive medical imaging apparatus it is proposed that the cleaning unit has at least one attachment element and that the receiving unit has at least one attachment element corresponding to the at least one attachment element of the cleaning unit, wherein the at least two attachment elements are embodied in such a way as to connect or disconnect an attachment mechanism during a vertical movement of the patient table. The vertical movement of the patient table preferably comprises a lifting movement in the direction of the gravitational force acting on the patient table or also in opposition to the gravitational force acting on the patient table. Preferably the attachment elements of the cleaning unit and of the patient table are embodied in such a way that, with a movement of the patient table upward, i.e. opposite to the gravitational force acting on the patient table, a coupling and/or attachment is made between the cleaning unit and the patient table. On the other hand. With a movement of the patient table downward, i.e. in the direction of the gravitational force acting on the patient table, an attachment between the cleaning unit and the patient table is released and/or removed. Here the at least one attachment element of the cleaning unit is in particular embodied as projecting and/or web shaped, so that with a movement upward of the patient table it engages into an attachment element of the patient table embodied as a recess. Preferably here the two attachment elements make a connection that can be embodied as a form fit in the direction of a longitudinal direction of the patient receiving area. For this purpose the attachment element of the patient table is arranged on a side pointing upward acting against the gravitation force acting on the patient table at the head end of the patient table.

This aspect of the disclosure makes possible a simple and in particular autonomous arrangement and/or attachment of the cleaning unit on the patient table. In particular in this case the cleaning unit can remain uncoupled from the patient table within the patient receiving area during a patient preparation, so that space available for the preparation continues to be available without restriction. An advantage of this aspect is that the cleaning unit can remain protected within the patient receiving area. Moreover in this way the cleaning unit is also arranged outside a field of view of a patient positioned on the patient table, so that the cleaning unit can also be arranged during a medical imaging examination on the end face side of the patient table.

BRIEF DESCRIPTION OF THE DRAWINGS

Further advantages, features and details of the disclosure emerge from the exemplary aspects described below as well as with the aid of the drawings.

In the drawings.

DETAILED DESCRIPTION

Figure 1:
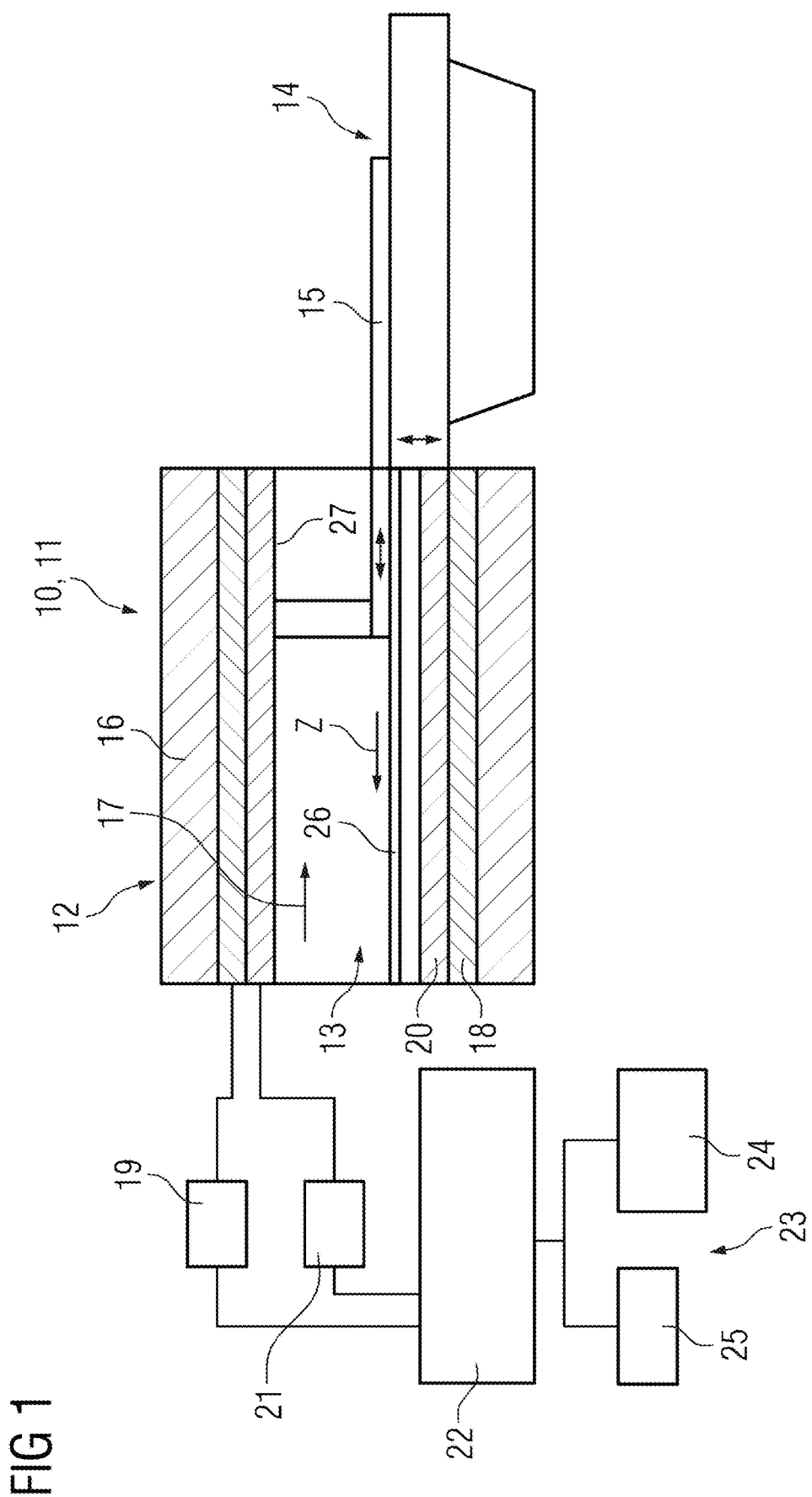
FIG. 1 shows an inventive medical imaging apparatus with a cleaning unit in a schematic diagram.

Shown schematically in FIG. 1 is a medical imaging apparatus 10. The medical imaging apparatus 10 in the present exemplary aspect is formed by a magnetic resonance apparatus 11, wherein the present disclosure is explained by way of example with the aid of the magnetic resonance apparatus 10. The present disclosure is not restricted however to an aspect of the medical imaging apparatus 10 as a magnetic resonance apparatus 11 and further aspects of the medical imaging apparatus 10 are always conceivable, such as for example s computed tomography apparatus and/or a PET apparatus etc.

The magnetic resonance apparatus 11 comprises a scanner unit 12 formed by a magnet unit. Moreover the magnetic resonance apparatus 10 has a patient receiving area 13 for receiving a patient. The patient receiving area 13 in the present exemplary aspect is embodied in a cylindrical shape and is surrounded in a circumferential direction by the scanner unit 12, in particular by the magnet unit, in a cylindrical shape. Basically however an aspect of the patient receiving area 13 that differs from this is always conceivable. The patient can be pushed and/or moved by means of a patient support apparatus 14 of the magnetic resonance apparatus 10 into the patient receiving area 13. For this purpose the patient support apparatus 14 has a patient table 15 embodied so that it can be moved within the patient receiving area 13. In particular here the patient table 15 is supported in a movable manner in the direction of a longitudinal extent of the patient receiving area 13 and/or in the z direction. To this end the medical imaging apparatus 10, in particular the magnetic resonance apparatus 11, has a rail system, which comprises two parallel rails 26. The individual rails 26 are arranged at the sides within the patient receiving area 13 for guidance of the patient table 15. The two rails 26 extend in this case along the entire patient receiving area 13.

The scanner unit 12, in particular the magnet unit, comprises a superconducting basic magnet 16 for creation of a strong and in particular constant basic magnetic field 17. Furthermore the scanner unit 12, in particular the magnet unit, has a gradient coil unit 18 for creation of magnetic field gradients, which are used for a spatial encoding during imaging. The gradient coil unit 18 is controlled by means of a gradient control unit 19 of the magnetic resonance apparatus 11. The scanner unit 12, in particular the magnet unit, furthermore comprises a radio frequency antenna unit 20 for creation of a polarization, which is set in the basic magnetic field 17 created by the basic magnet 16. The radio frequency antenna unit 20 is controlled by a radio frequency antenna control unit 21 of the magnetic resonance apparatus 11 and radiates radio frequency magnetic resonance sequences into the patient receiving area 13 of the magnetic resonance apparatus 11.

For control of the basic magnet 16 of the gradient control unit 19 and for control of the radio frequency antenna control unit 21 the magnetic resonance apparatus 11 has a system control unit 22. The system control unit 22 controls the magnetic resonance apparatus 11 centrally, such as for example the carrying out of a prespecified imaging gradient echo sequence. Moreover the system control unit 22 comprises an evaluation unit not shown in any greater detail for evaluation of medical imaging data that is acquired during the magnetic resonance examination.

Furthermore the magnetic resonance apparatus 10 comprises a user interface 23, which is connected to the system control unit 22. Control information such as for example imaging parameters, as well as reconstructed magnetic resonance images can be displayed on a display unit 24, for example on at least one monitor, of the user interface 23 for a medical operator. The user interface 23 furthermore has an input unit 25, by means of which information and/or parameters can be entered during a measurement process by the medical operator.

The magnetic resonance apparatus 10 shown can of course comprise further components that magnetic resonance apparatuses 10 usually comprise. The general way in which a magnetic resonance apparatus 10 functions is moreover known to the person skilled in the art, so that a more detailed description of the further components will be dispensed with here.

The magnetic resonance apparatus moreover has a cleaning unit 100, 200, 300, 400, 500, 600, which is embodied for cleaning a housing 27 surrounding the patient receiving area 13 of the magnetic resonance apparatus 11. The housing 27 surrounding the patient receiving area 13 is embodied as a single part and/or in one piece in the present exemplary aspect with a side of the radio frequency antenna unit 20 facing toward the patient receiving area 13. Moreover the housing 27 surrounding the patient receiving area 13 can also comprise a housing shell.

The cleaning unit 100, 200, 300, 400, 500, 600 has at least one cleaning element 101, 201, 301, 401, 501, 601. In FIGS. 1 to 14 the cleaning unit 100, 200, 300, 400, 500, 600 has a single cleaning element 101, 201, 301, 401, 501, 601. It is however also conceivable for the cleaning unit 100, 200, 300, 400, 500, 600 to have two or more cleaning elements 101, 201, 301, 401, 501, 601. These can also be embodied identically and be arranged one after another for increasing the success of the cleaning.

Figure 2:
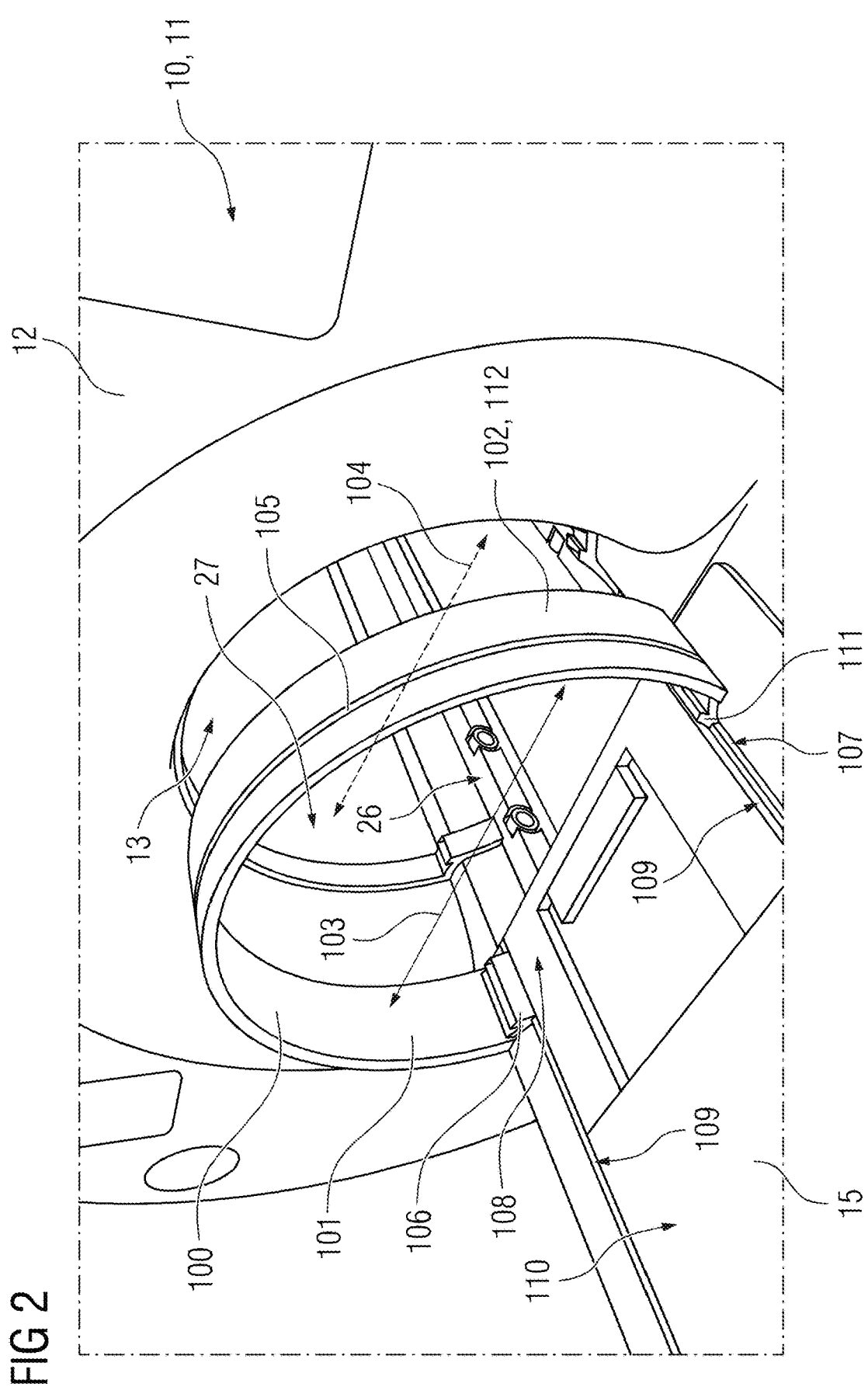
FIG. 2 shows a first exemplary aspect of a cleaning unit on a patient table of the medical imaging apparatus.

Shown in FIG. 2 is the medical imaging apparatus 10, in particular the magnetic resonance apparatus 11, with a first exemplary aspect of the cleaning unit 100. The cleaning unit 100 has a cleaning element 101 with an annular carrier structure 102. The cleaning element 101, in particular the annular carrier structure 102, is adapted to a circumference, in particular to an inner circumference, of the housing 13 surrounding the patient receiving area 13. The cleaning element 101 comprises a diameter 103, in particular an outer diameter, of the at least one value of the diameter 104, in particular of the inner diameter, of the housing 27 surrounding the patient receiving area 13. Moreover the diameter 103, in particular the outer diameter, of the cleaning element 101 can be embodied greater by a maximum of 1 mm, preferably by a maximum of 2 mm and preferably by a maximum of 3 mm than the diameter 104, in particular the inner diameter, of the housing 27 surrounding the patient receiving area 13.

Furthermore the cleaning unit 101 has two base elements 106, which are embodied for an arrangement and/or positioning of the cleaning elements 101, in particular of the annular carrier structure 102, within the patient receiving area 13. The two base elements 106 are embodied here for an arrangement and/or attachment of the cleaning unit 100 to the patient table 15. For arrangement of the cleaning unit 100 on the patient table 15 the patient table 15 has a receiving unit 107, wherein the receiving unit 107 is arranged at a head end 108 of the patient table 15. The head end 108 of the patient table 15 here comprises an end area of the patient table 15, which is introduced first into the patient receiving area 13 when the patient table 15 is introduced into the patient receiving area 13.

The patient table 15 furthermore has two attachment rails 109, which are embodied for attachment of accessory units. The two attachment rails 109 are arranged on opposite side areas of the patient table 15, wherein a support area 110 for supporting and/or positioning of the patient is arranged between the two attachment rails 109. The receiving unit 107 for arrangement of the cleaning unit 100 on the patient table 15 has the two attachment rails 109 in this case, in particular an area of the attachment rails 109 in each case facing toward the head end 108 of the patient table 15. For an arrangement of the cleaning unit 100 on the two attachment rails 109 the cleaning unit 100 has two attachment elements 111 corresponding to the attachment rails 109. The two attachment elements 111 are arranged on the two base elements 106, wherein one attachment element 109 is arranged on a base element 106 in each case. In this case the two base elements 109 are also arranged on opposite sides of the cleaning unit 100.

Moreover the cleaning element 101 has a cleaning covering 105. The cleaning covering 105 in the present exemplary aspect comprises a wiping lip, which preferably comprises an elastic material. The cleaning covering 105, in particular the wiping lip, is arranged here on a side pointing outward, in particular on a side of the annular carrier structure 102 facing toward the housing 27 surrounding the patient receiving area 13. For this purpose the annular carrier structure 102 can also comprise on its outer side a slot-shaped recess for accepting the cleaning covering 105, in particular the wiping lip. Preferably here the cleaning covering 105, in particular the wiping lip, is removable, arranged for example by a hook and loop connection and/or by a form-fit receiving slot, on the outer side of the annular carrier structure 102.

The annular carrier structure 102 in the present exemplary aspect can in this case have a single ring element 112, wherein the ring element is arranged on the two base elements. Preferably the annular carrier structure 102 can also have two ring elements, wherein the two ring elements are arranged in a first end area on one of the two base elements 106 in each case. The two ring elements can in this be embodied at least partly in a movable manner in relation to one another at a second end area facing away from the base elements 106, so that the annular carrier structure 102 is pressed inward when the cleaning unit 100 is introduced into the patient receiving area 13. Preferably in this case the annular carrier structure 102 has a diameter, in particular an outer diameter, which at least corresponds to the diameter 104, in particular the inner diameter, of the housing 27 surrounding the patient receiving area 13 or also is larger by a maximum of 3 mm than the diameter 104, in particular the inner diameter, of the housing 27 surrounding the patient receiving area 13.

The arrangement of the cleaning covering 105, in particular of the wiping lip, on the outer side of the annular carrier structure 102 means that the cleaning element 101 thus has a larger outer diameter than the inner diameter of the housing 27 surrounding the patient receiving area 13. A diameter of the annular carrier structure 102 can moreover also be dependent on a thickness of the cleaning covering 105, in order to achieve a desired diameter 103 of the cleaning element 101. The effect of this is that, after an introduction of the cleaning unit 100 into the patient receiving area 13, the cleaning element 101 rests with a force against the housing 27 surrounding the patient receiving area 13. Preferably here the cleaning element 101 rests with a force of 4 N to 6 N against the housing 27 surrounding the patient receiving area 13, so that a sufficiently high pressure for a mechanical cleaning is present, but a movement of the cleaning unit 100 through the patient receiving area 13 is also possible.

Figure 3:
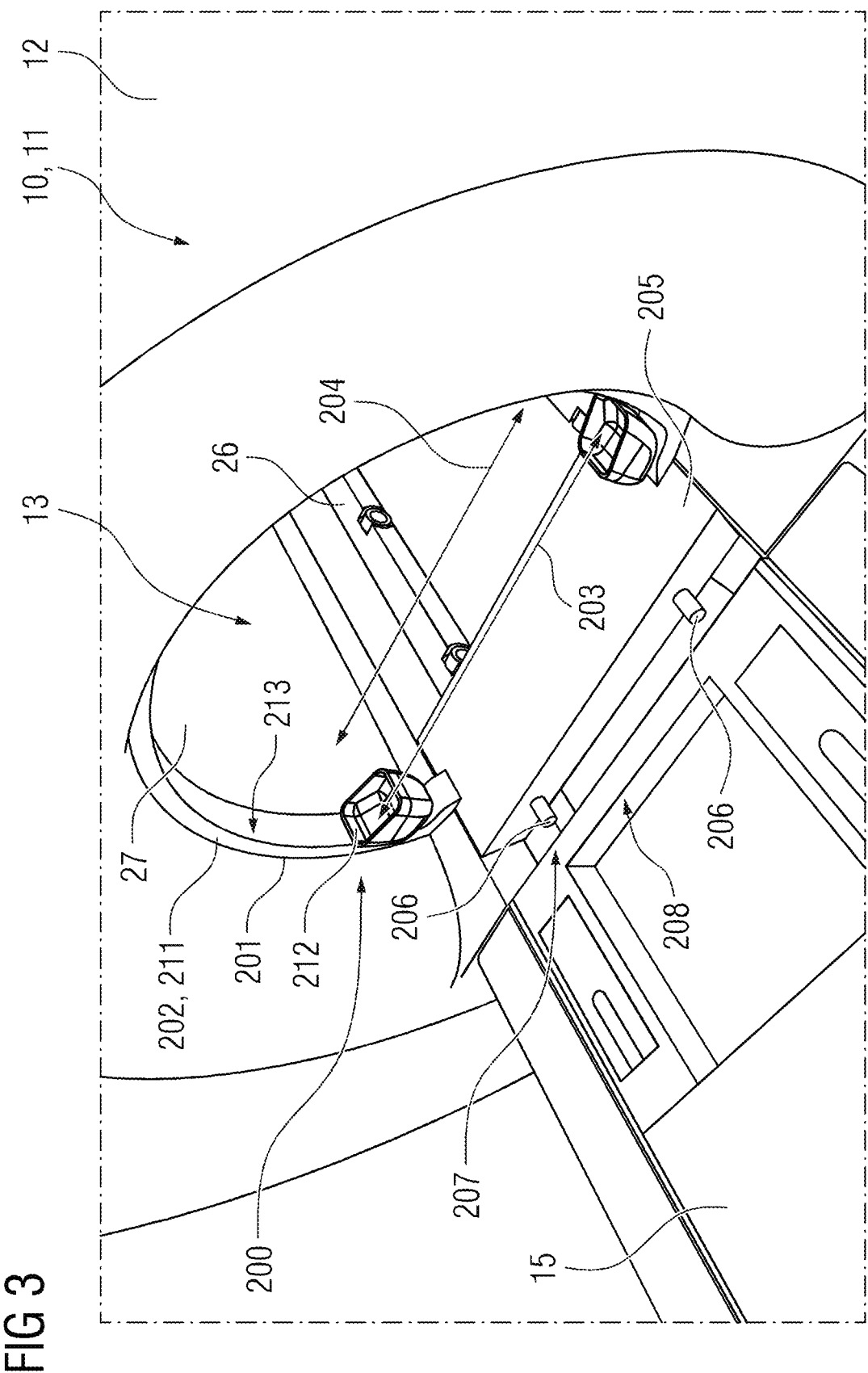
FIG. 3 shows a second exemplary aspect of the cleaning unit on the patient table of the medical imaging apparatus in a first view.
Figure 4:
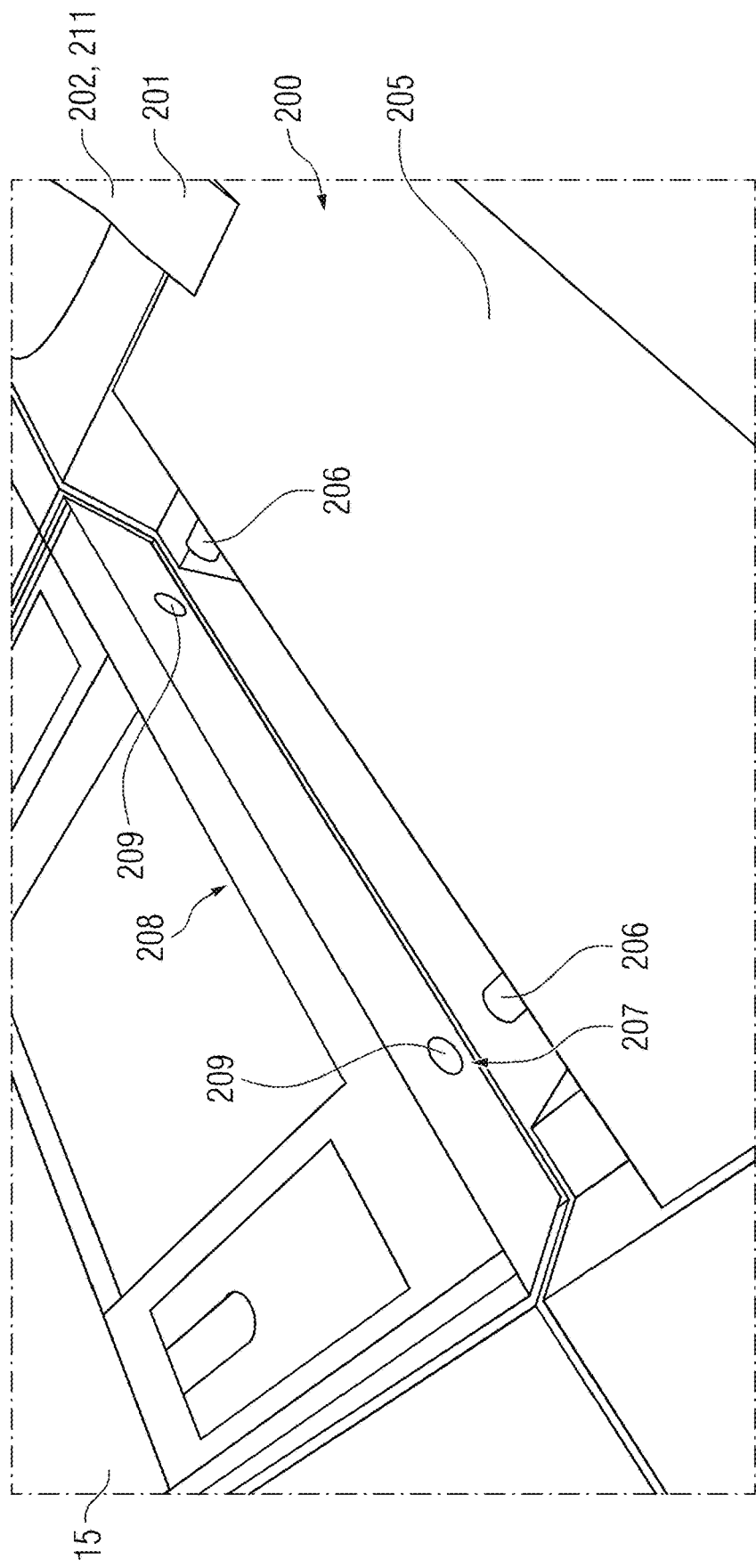
FIG. 4 shows the second exemplary aspect of the cleaning unit in a second view.
Figure 5:
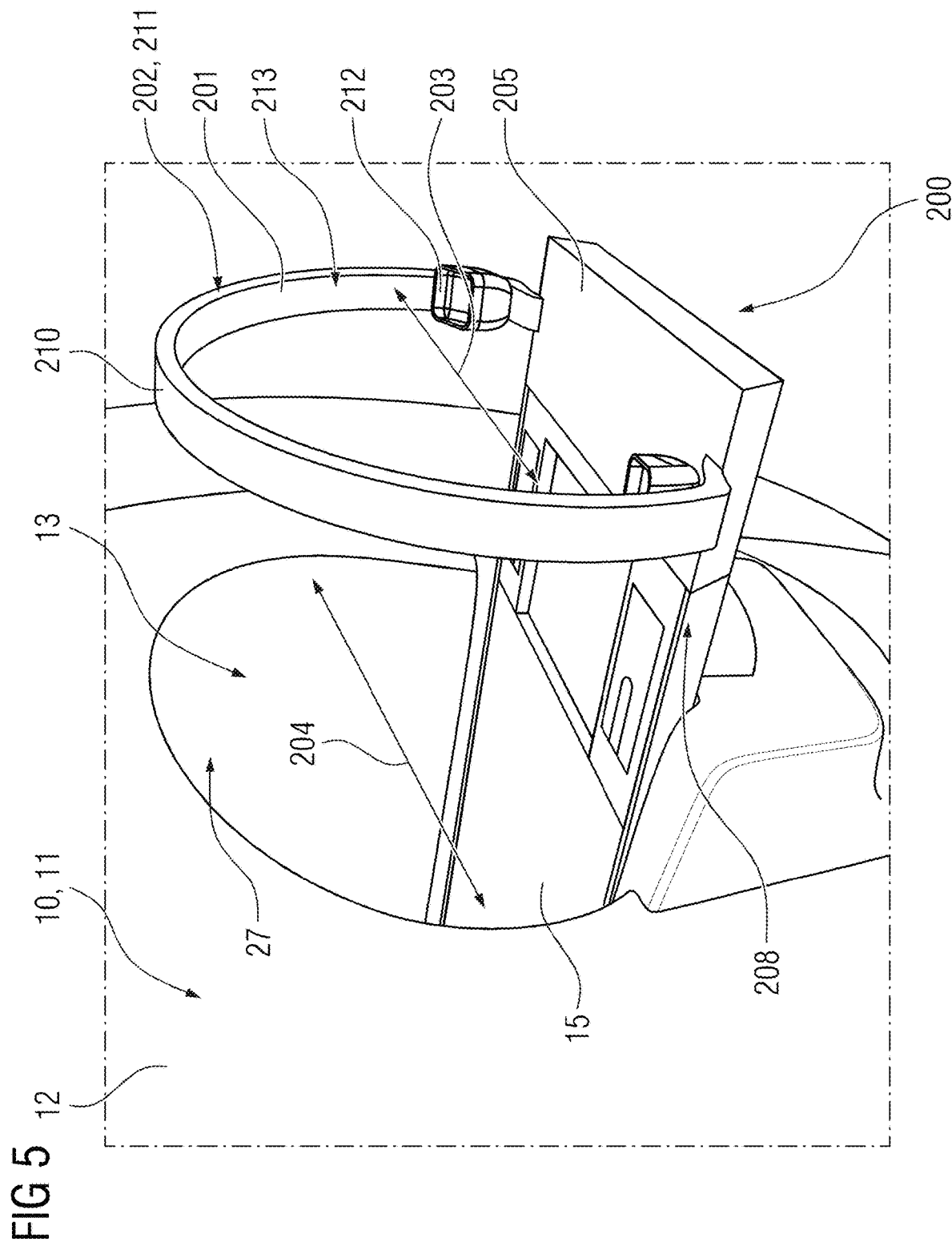
FIG. 5 shows the second exemplary aspect of the cleaning unit in a third view.

Shown in FIGS. 3 to 5 is a second exemplary aspect of the cleaning unit 200. Components, features and functions that essentially remain the same are basically labeled with the same reference characters. The description given below essentially restricts itself to the differences from the exemplary aspect in FIG. 2, wherein with regard to components, features and functions that essentially remain the same the reader is referred to the description of the exemplary aspect in FIG. 2.

Shown in FIGS. 3 to 5 is the medical imaging apparatus 10, in particular the magnetic resonance apparatus 11, with a second exemplary aspect of the cleaning unit 200. The cleaning unit 200 has a cleaning element 201 with an annular carrier structure 202. The cleaning element 201, in particular the annular carrier structure 202, is adapted to a circumference, in particular to an inner circumference, of the housing 27 surrounding the patient receiving area 13. In this case the cleaning element 201 comprises a diameter 203, in particular an outer diameter, which at least corresponds to a value of the diameter 204, in particular of the inner diameter, of the housing 27 surrounding the patient receiving area 13. Moreover the diameter 203, in particular the outer diameter, of the cleaning element 201 can be embodied greater by a maximum of 1 mm, preferably by a maximum of 2 mm and preferably by a maximum of 3 mm than the diameter 204, in particular the inner diameter, of the housing 27 surrounding the patient receiving area 13.

Moreover the cleaning unit 200 has a base element 205, which is embodied for an arrangement of the cleaning element 201, in particular of the annular carrier structure 202, within the patient receiving area 13. In this case the cleaning unit 200 is able to be arranged by means of the base element 205 on the rail system, in particular on the two rails 26 of the rail system. The base element 205 is embodied in this case in such a way that it rests on both sides on one of the two rails 26 of the rail system. Moreover the base element 205 comprises attachment elements 206 for an attachment and/or coupling of the cleaning unit 200 to the patient table 15. In the present exemplary aspect the base element 205 comprises two attachment elements 206, which each extend in a web shape away from the base element 205 in the direction of the patient table 15. The two attachment elements 206 moreover have a round cross section (FIG. 3).

For arrangement of the cleaning unit 200 on the patient table 15 the patient table 15 has a receiving unit 207, wherein the receiving unit 207 is arranged at a head end 208 of the patient table 15 (FIG. 4). The receiving unit 207 in this case has two attachment elements 209, which are embodied to correspond to the two attachment elements 206 of the base unit 205. The two attachment elements 209 of the receiving unit 207 are arranged on the end face side of the patient table 15. For a coupling and/or arrangement of the cleaning unit 200 to the patient table 15, the cleaning unit 200 is already located within the patient receiving area 13, in particular in an introduction region of the patient receiving area 13, on the rails 26. When the patient table 15 is moved in the horizontal direction into the patient receiving area 13, the cleaning unit 200 in this case couples to the patient table 15 and is pushed and/or drawn by means of the patient table 15 for a cleaning process through the patient receiving area 13. The attachment elements 206 of the base element 205 and/or the attachment elements 209 of the patient table 15 can in this case moreover comprise a latching element and/or a clamping element, which with a movement of the patient table 15 against the inward direction prevents a release of the cleaning unit 200 from the patient table 15. In this case the cleaning unit 200, for a cleaning of the housing 27 surrounding the patient receiving area 13, can also leave the patient receiving area 13 on a rear side of the medical imaging apparatus 10 and in this case is held by means of the attachment elements 206, 209 of the patient table 15 (FIG. 5). Moreover the attachment mechanism between the cleaning unit 200 and the patient table 15 is embodied in such a way that, when the patient table 15 leaves the patient receiving area 13, in particular at the introduction opening of the patient receiving area 13, the attachment mechanism is released and the cleaning unit 200 remains in the patient receiving area 13.

Moreover the cleaning element 201 has a cleaning covering 210 (FIG. 5). The cleaning covering 210 comprises in the present exemplary aspect a textile fabric, such as for example a non-woven material. The cleaning covering 210 here is arranged on a side pointing outward, in particular on a side facing toward the housing 27 surrounding the patient receiving area 13, of the annular carrier structure 202. For this purpose the annular carrier structure 202 can also comprise on its outer side a slot-shaped recess for accepting the cleaning covering 210. Preferably here the cleaning covering 210, in particular the non-woven material, is arranged in a removable manner, for example by a hook and loop fastening and/or by a form-fit receiving slot, on the outer side of the annular carrier structure 202.

The annular carrier structure 202 in the present exemplary aspect can in this case have a single ring element 211, wherein the ring element 211 is arranged on the base element 205. Preferably the annular carrier structure 202 can also have two ring elements, wherein the two ring elements are arranged in each case on a first end area on the base element 205. The two ring elements in this case can be embodied in a movable manner at least partly in relation to one another at a second end area facing away from the base element 205, so that the annular carrier structure 202 is pushed inward when the cleaning unit 200 is introduced into the patient receiving area 13. Preferably in this case the annular carrier structure 202 has a diameter, in particular an outer diameter, which at least corresponds to the diameter 204, in particular the inner diameter, of the housing 27 surrounding the patient receiving area 13 or also is a maximum of 3 mm greater than the diameter 204, in particular the inner diameter, of the housing 27 surrounding the patient receiving area 13.

The arrangement of the cleaning covering 210 on the outer side of the annular carrier structure 202 thus means that the cleaning element 201 has a larger outer diameter than the inner diameter of the housing 27 surrounding the patient receiving area 13. The effect of this is that after an introduction of the cleaning unit 200 into the patient receiving area 13, the cleaning element 201 rests with a force against the housing 27 surrounding the patient receiving area 13, as has already been described for FIG. 2, to which the reader is herewith referred.

Furthermore the cleaning unit 200 comprises a receiving element 212 for receiving a cleaning agent (FIGS. 3 and 5). The receiving element 212 for receiving the cleaning agent is arranged in this case on an inner side 213 of the annular carrier structure 202. The receiving element 212 can for example comprise a holder for accepting a commercially available cleaning agent container with cleaning agent and/or a commercially available disinfection agent container with disinfection agent. Moreover the annular carrier structure 202 can also comprise a cleaning agent channel not shown in any greater detail here and/or a cleaning agent hose for distribution of the cleaning agent to the cleaning covering 210.

Figure 6:
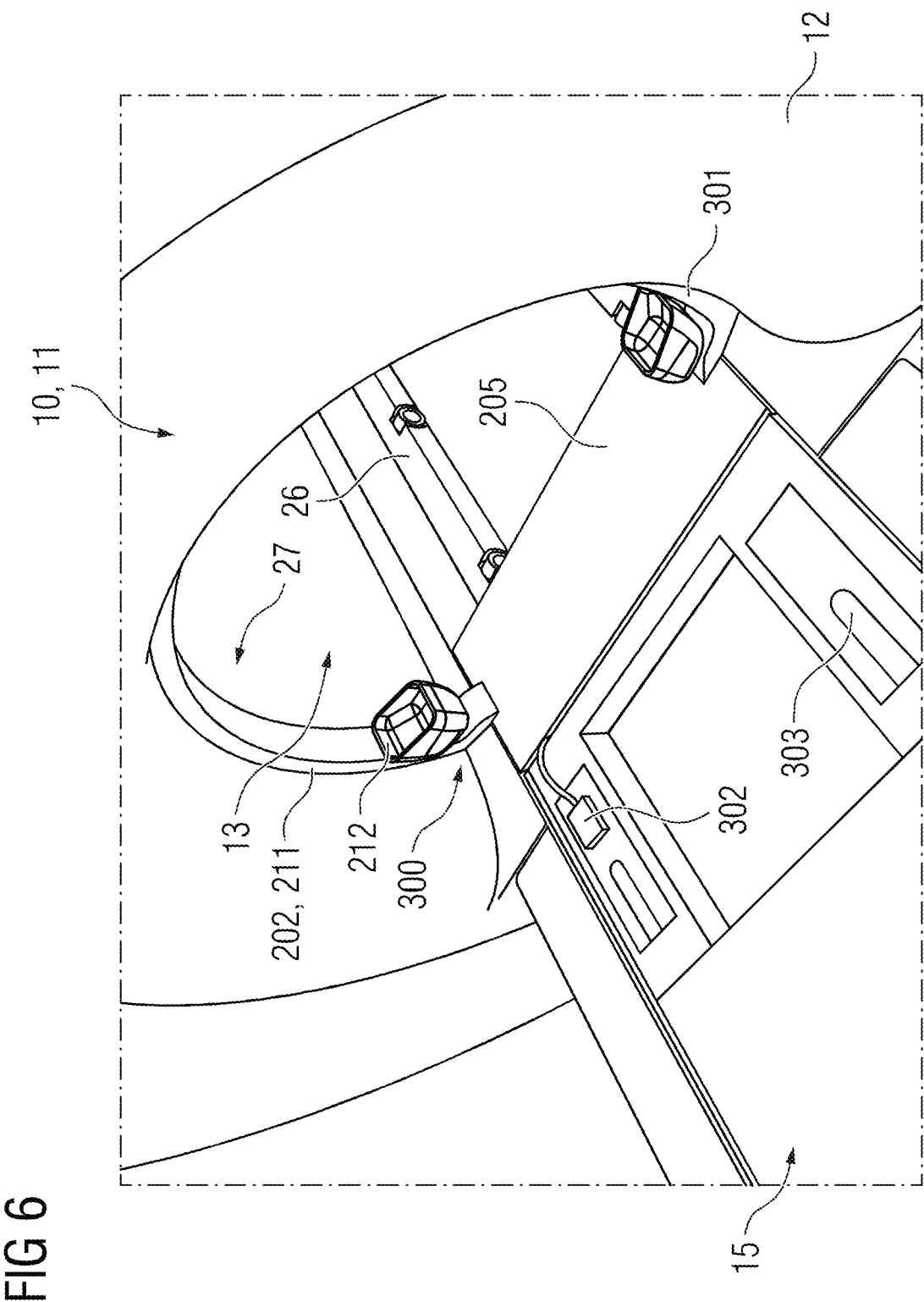
FIG. 6 shows a third exemplary aspect of the cleaning unit on the patient table of the medical imaging apparatus.

Shown in FIG. 6 is a third exemplary aspect of the cleaning unit 300. Components, features and functions that essentially remain the same are basically labeled with the same reference characters. The description given below essentially restricts itself to the differences from the exemplary aspect in FIGS. 3 to 5, wherein with regard to components, features and functions that essentially remain the same the reader is referred to the description of the exemplary aspect in FIGS. 3 to 5.

The exemplary aspect in FIG. 6 differs from the exemplary aspect in FIGS. 3 to 5 in that the cleaning unit 300 has an electrical connection element 302. In this aspect the electrical connection element 302 is embodied identical in construction to a coil plug connector of a local radio frequency coil. Moreover the patient table 15 also has a connecting socket 303 for making electrical contact with a local radio frequency coil. The electrical connection element 302 of the cleaning unit 300 in this case is embodied compatible with the connecting socket 303 of the patient table 15. For an electrical contacting, in particular a control of the cleaning unit 300 and/or an acquisition of cleaning data etc., the electrical connection element 302 is plugged into the connecting socket 303.

A further aspect of the cleaning unit 300 corresponds to the versions of the exemplary aspect in FIGS. 3 to 5, to which the reader is herewith referred.

Figure 7:
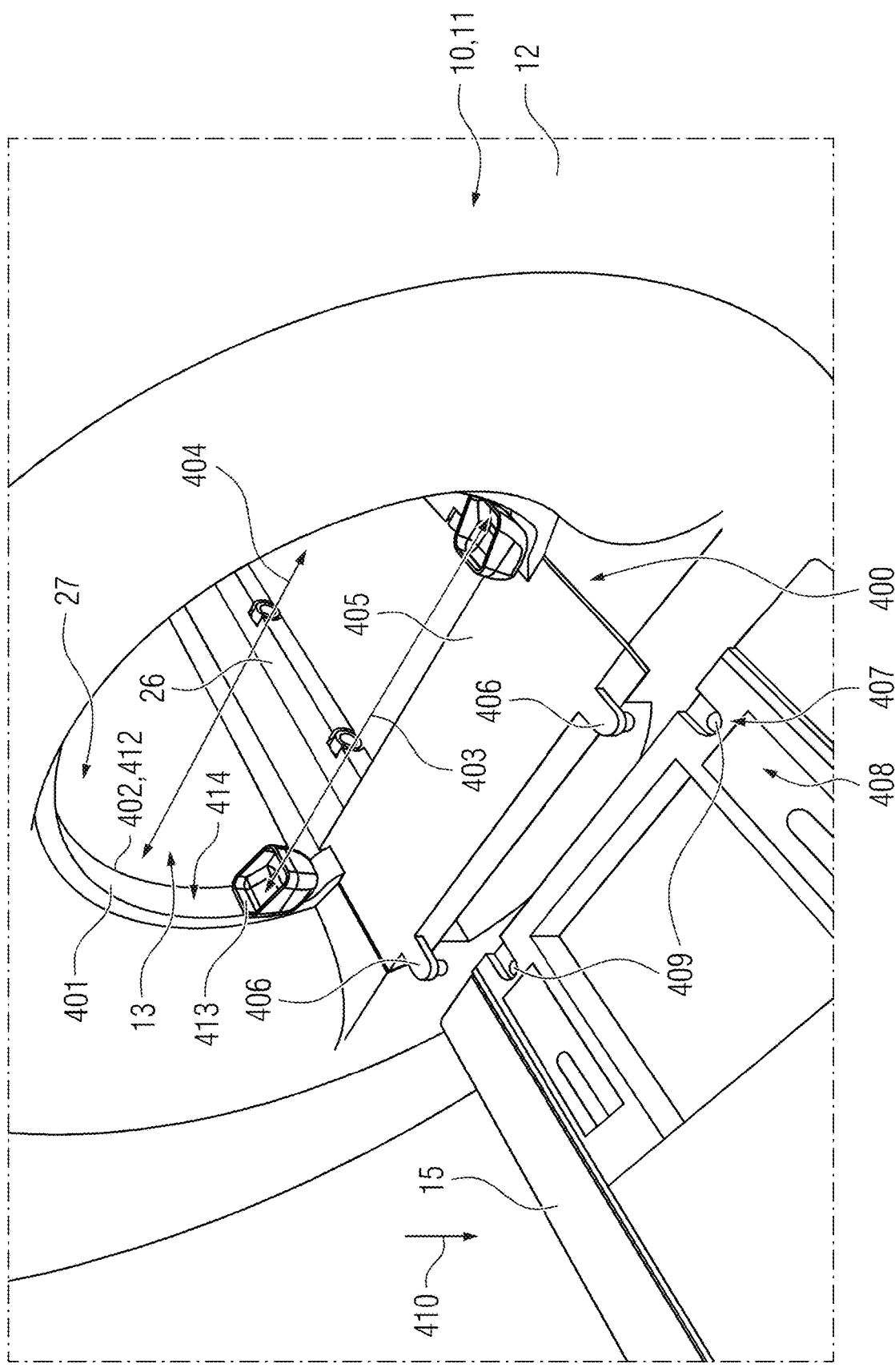
FIG. 7 shows a fourth exemplary aspect of the cleaning unit on the patient table of the medical imaging apparatus in a first view.
Figure 8:
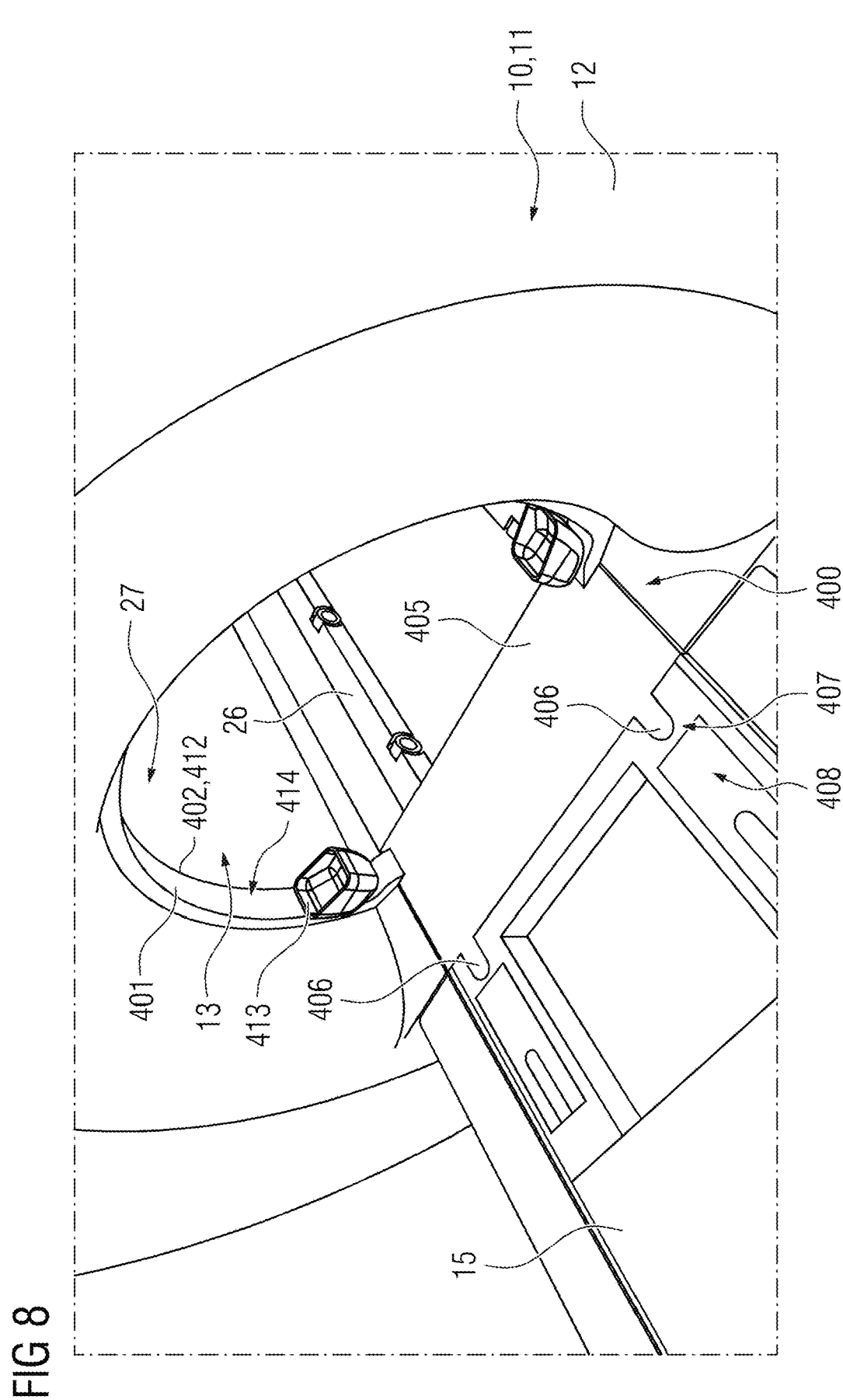
FIG. 8 shows the fourth exemplary aspect of the cleaning unit in a second view.
Figure 9:
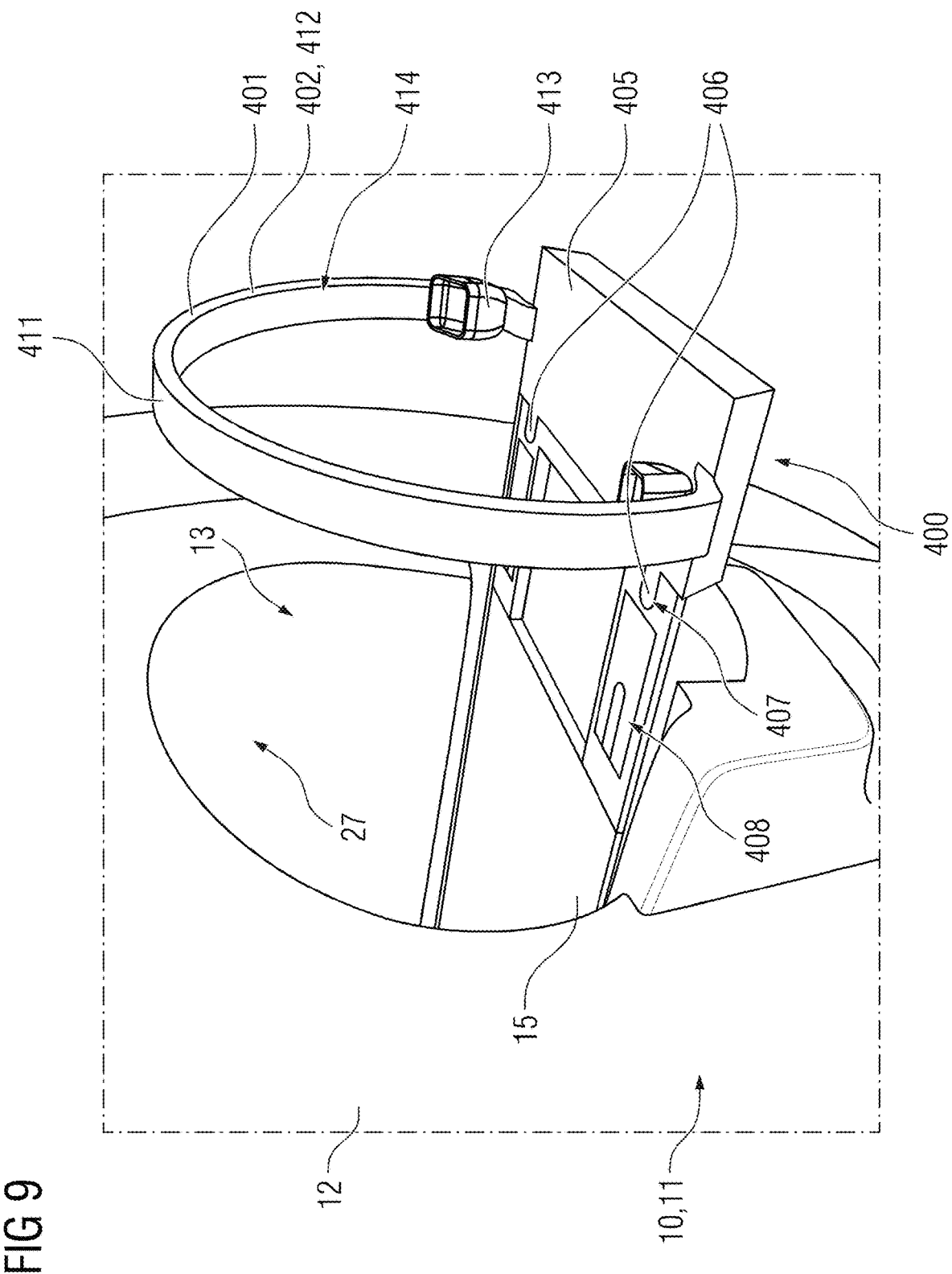
FIG. 9 shows the fourth exemplary aspect of the cleaning unit in a third view.

Shown in FIGS. 7 to 9 is a fourth exemplary aspect of the cleaning unit 400. Components, features and functions that essentially remain the same are basically labeled with the same reference characters. The description given below essentially restricts itself to the differences from the exemplary aspect in FIGS. 2 to 6, wherein with regard to components, features and functions that essentially remain the same the reader is referred to the description of the exemplary aspect in FIGS. 2 to 6.

Shown in FIGS. 7 to 9 is the medical imaging apparatus 10, in particular the magnetic resonance apparatus 11, with a fourth exemplary aspect of the cleaning unit 400. The cleaning unit 400 has a cleaning element 401 with an annular carrier structure 402. The cleaning element 401, in particular the annular carrier structure 402, is adapted to a circumference, in particular to an inner circumference, of the housing 27 surrounding the patient receiving area 13. In this case the cleaning element 401 comprises a diameter 403, in particular an outer diameter, which corresponds to at least a value of the diameter 404, in particular of the inner diameter, of the housing 27 surrounding the patient receiving area 13. Moreover the diameter 403, in particular the outer diameter, of the at least one cleaning element 401 can be embodied larger by a maximum of 1 mm, preferably by a maximum of 2 mm and preferably by a maximum of 3 mm than the diameter 404, in particular the inner diameter, of the housing 27 surrounding the patient receiving area 13.

Furthermore the cleaning unit 400 has a base element 405, which is embodied for an arrangement of the cleaning elements 401, in particular of the annular carrier structure 402, within the patient receiving area 13. In this case the cleaning unit 400 is able to be arranged by means of the base element 405 on the rail system, in particular on the two rails 26 of the rail system. The base element 405 in this case is embodied in such a way that it rests on both sides on one of the two rails 26 of the rail system. Moreover the base element 405 comprises attachment elements 406 for an attachment and/or coupling of the cleaning unit 400 to the patient table 15. In the present exemplary aspect the base element 405 comprises two attachment elements 406. The two attachment elements 406 are embodied in an L shape and each have a web element, which extends in the shape of a web from the base element 405 in the direction of the patient table 15. The two web elements have a planar and/or flat surface with the base element 405. Moreover the two attachment elements 406 each have a pin, which is arranged at an end of the web elements facing away from the base element 405. The pins extend downward in this case at right angles to the web elements, in particular in the direction of gravity (FIG. 7).

For arrangement of the cleaning unit 400 on the patient table 15 the patient table 15 has a receiving unit 407, wherein the receiving unit 407 is arranged at a head end 408 of the patient table 15. The receiving unit 407 in this case has two attachment elements 409, which are embodied to correspond to the two attachment elements 406 of the base unit 405. The two attachment elements 409 of the receiving unit 407 are arranged on the end face side of the patient table 15. In this case the two attachment elements 409 of the receiving unit 407 are embodied in an L shape for receiving the attachment elements 406 of the cleaning unit 400 (FIG. 7).

For a coupling and/or arrangement of the cleaning unit 400 to the patient table 15 the cleaning unit 400 is already located within the patient receiving area 13, in particular arranged in an introduction area of the patient receiving area 13, on the rails 26. An attachment mechanism and/or coupling mechanism between the patient table 15, in particular the receiving unit 407 of the patient table 15, and the cleaning unit 400, in particular the attachment elements 406 of the cleaning unit 400, is embodied in this case such that, with a vertical movement of the patient table 15, an attachment and/or coupling between the patient table 15 and the cleaning unit 400 is made or released. A vertical movement of the patient table 15 is only possible for example when the patient table 15 is arranged completely outside of the patient receiving area 13. The vertical movement of the patient table 15 preferably comprises a lifting movement in the direction 410 of the gravitational force acting on the patient table 15 or also in the opposite direction to the gravitational force acting on the patient table 15. With a movement of the patient table 15 upward, i.e. in the opposite direction to the gravitational force acting on the patient table 15, the attachment elements 406 of the cleaning unit 400 engage in the attachment elements 409 of the receiving unit 407 and a coupling and/or attachment takes place between cleaning unit 400 and the patient table 15. Preferably here the attachment elements 405, 409 make a connection, which is embodied as a form fit in the direction of a longitudinal direction of the patient receiving area 13, so that after a coupling and/or attachment of the cleaning unit 400 to the patient table 15 the cleaning unit 400 is moved as a result of a horizontal movement of the patient table 15 through the patient receiving area 13. In this case the cleaning unit 400 for cleaning of the housing 27 surrounding the patient receiving area 13 can also leave the patient receiving area 13 at a rear side of the medical imaging apparatus 10 and in this case is held by means of the attachment elements 406, 409 of the patient table 15 (FIG. 9). With a movement of the patient table 15 downward, i.e. in the direction 410 of the force of gravity acting on the patient table 15, on the other hand an attachment between the cleaning unit 400 and the patient table 15 is released, so that the cleaning unit 400 remains in the patient receiving area 13.

Moreover the cleaning element 401 has a cleaning covering 411. The cleaning covering 411 comprises in the present exemplary aspect comprises a textile fabric, such as for example a non-woven material. An aspect, arrangement and functioning of the cleaning covering 411 correspond here to what has been described for FIGS. 3 to 5, to which the reader is herewith referred (FIG. 9).

The annular carrier structure 402 in the present exemplary aspect can in this case have a single ring element 412, wherein the ring element 412 is arranged on the base element 405. Preferably the annular carrier structure 402 can also have two ring elements, wherein the two ring elements are each arranged at a first end area on the base elements 405. The two ring elements can be embodied in this case to be at least partly movable in relation to one another at a second end area facing away from the at least one base element 405, so that the annular carrier structure 402 is pushed inward when the cleaning unit 400 is introduced into the patient receiving area 13. Preferably in this case the annular carrier structure 402 has a diameter, in particular an outer diameter, which at least corresponds to the diameter 404, in particular the inner diameter, of the housing 27 surrounding the patient receiving area 13 or also is greater by a maximum of 3 mm than the diameter 404, in particular the inner diameter, of the housing 27 surrounding the patient receiving area 13.

The arrangement of the cleaning covering 411 on the outer side of the annular carrier structure 402 thus means that the cleaning element 401 has a larger outer diameter than the inner diameter of the housing 27 surrounding the patient receiving area 13. The effect of this is that, after an introduction of the cleaning unit 400 into the patient receiving area 13, the cleaning element 401 rests with a force against the housing 27 surrounding the patient receiving area 13, as has already been described for FIG. 2, to which the reader is herewith referred.

Furthermore the cleaning unit 400 comprises a receiving element 413 for receiving a cleaning agent. The receiving element 413 for receiving the cleaning agent is arranged in this case on an inner side 414 of the annular carrier structure 402. The receiving element 413 can for example comprise a holder for receiving a commercially available cleaning agent container with cleaning agent and/or a commercially available disinfection agent container with disinfection agent. Moreover the annular carrier structure 402 here can also comprise a cleaning agent channel and/or a cleaning agent tube not shown in any greater detail for distribution of the cleaning agent at the cleaning covering 411.

Furthermore the cleaning unit 400 can also have an electrical connection element, wherein an electrical connection element is not shown in greater detail in FIGS. 7 to 9.

An aspect and/or functioning of an electrical connection element correspond in this case to the description given for FIG. 6, to which the reader is herewith referred.

Shown in FIGS. 10 to 13 is a fifth exemplary aspect of the cleaning unit 500. Components, features and functions that essentially remain the same are basically labeled with the same reference characters. The description given below essentially restricts itself to the differences from the exemplary aspect in FIGS. 2 to 9, wherein with regard to components, features and functions that essentially remain the same the reader is referred to the description of the exemplary aspect in FIGS. 2 to 9.

The cleaning unit 500 in FIGS. 10 to 13 has a cleaning element 501 with an annular carrier structure 502. The cleaning element 501, in particular the annular carrier structure 502, is adapted to a circumference, in particular to an inner circumference, of the housing 27 surrounding the patient receiving area 13. In this case the cleaning element comprises 501 a diameter, in particular an outer diameter, which a least corresponds to the value of the diameter, in particular of the inner diameter, of the housing 27 surrounding the patient receiving area 13. Moreover the diameter, in particular the outer diameter, of the cleaning element 501 can be embodied greater by a maximum of 1 mm, preferably by a maximum of 2 mm and preferably by a maximum of 3 mm than the diameter, in particular the inner diameter, of the housing 27 surrounding the patient receiving area 13.

Figure 10:
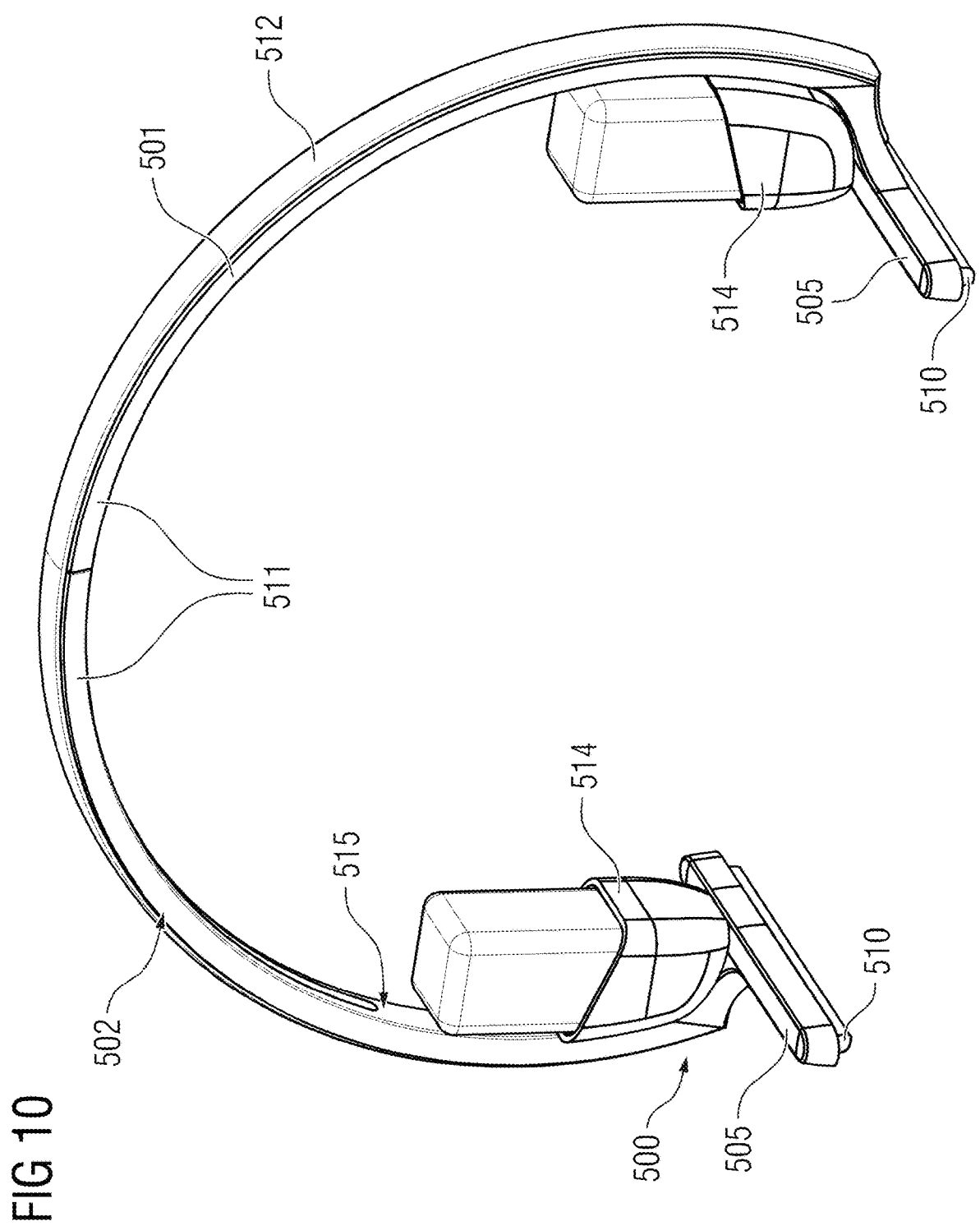
FIG. 10 shows a fifth exemplary aspect of the cleaning unit on the patient table of the medical imaging apparatus in a first view.
Figure 11:
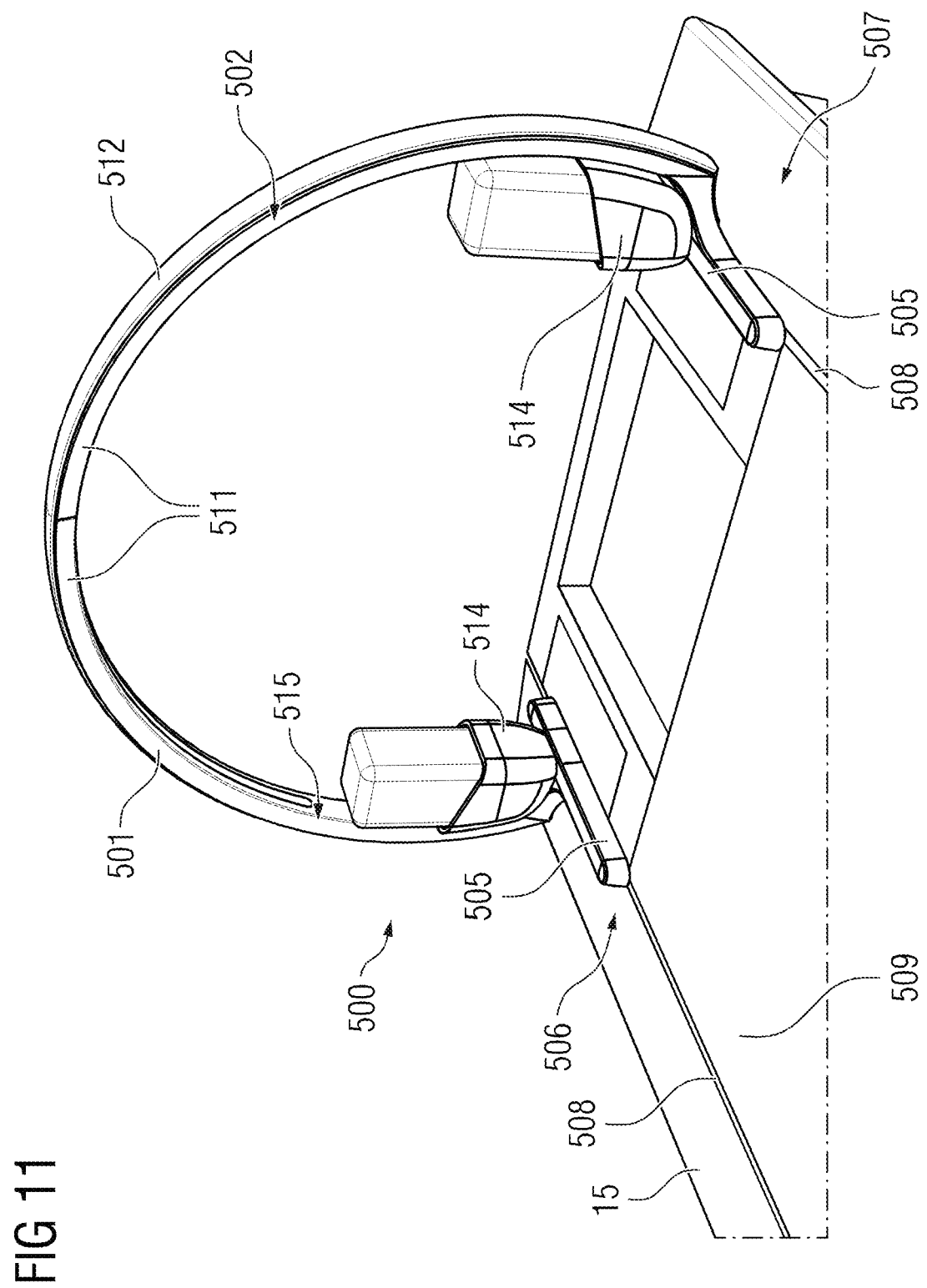
FIG. 11 shows the fifth exemplary aspect of the cleaning unit in a second view.
Figure 12:
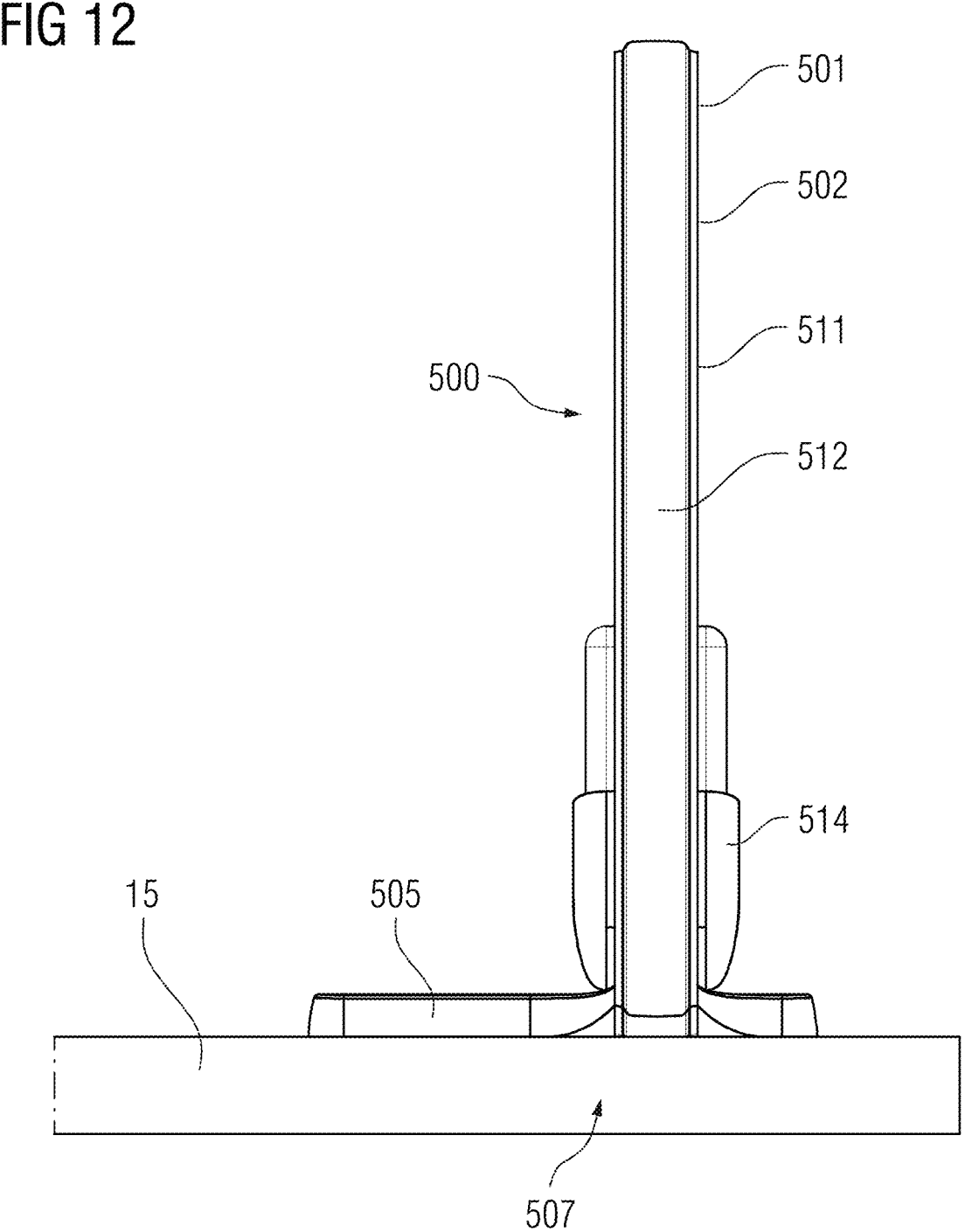
FIG. 12 shows the fifth exemplary aspect of the cleaning unit in a third view.

Furthermore the cleaning unit 500 has two base elements 505, which are embodied for an arrangement and/or positioning of the cleaning element 501, in particular of the annular carrier structure 502, within the patient receiving area 13. The two base elements 505 here are embodied for an arrangement and/or attachment of the cleaning unit 500 on the patient table 15 (FIG. 10-12). For arrangement of the cleaning unit 500 on the patient table 15 the patient table 15 has a receiving unit 506, wherein the receiving unit 506 is arranged at a head end 507 of the patient table 15 (FIG. 11).

The patient table 15 furthermore has two attachment rails 508, which are embodied for an attachment of accessory units (FIG. 10). The two attachment rails 508 are arranged at opposite side areas of the patient table 15, wherein a support area 509 for supporting and/or positioning of the patient is arranged between the two attachment rails 508. The receiving unit 506 for arrangement of the cleaning unit 500 on the patient table 15 has the two attachment rails 508 in this case, in particular one area of the two attachment rails 109 facing toward the head end 507 of the patient table 15 in each case. For an arrangement of the cleaning unit 500 on the two attachment rails 508 the cleaning unit 500 has two attachment elements 510 corresponding to the attachment rails 508. The two attachment elements 510 are arranged on the two base elements 505, wherein one attachment element 510 is arranged on a base element 505 in each case. In this case the two base elements 505 are also arranged on opposite sides of the cleaning unit 100.

The annular carrier structure 502 in the present exemplary aspect has two ring elements 511 (FIGS. 10 and 11). The two ring elements 511 are each arranged at a first end area on one of the two base elements 505. At a second end area, in particular an end area facing away from the base elements 505, the two ring elements 511 of the annular carrier structure 502 are arranged at least partly able to move in relation to one another. The end areas of the two ring elements 511 facing away from the base elements 505 can be embodied in this case resting against one another and/or at least partly overlapping. In the present exemplary aspect the two ring elements 511 are arranged and/or embodied essentially mirror-symmetrically in relation to one another.

If the cleaning unit 500 and thus also the annular carrier structure 502 is located outside of the patient receiving area 13, the two ring elements 511 are preferably in a relaxed state. In this relaxed state a diameter, in particular an outer diameter, of the cleaning elements 501 has at least the same value or a greater value than a diameter, in particular inner diameter, of the housing 27 surrounding the patient receiving area 13. If on the other hand the cleaning unit 500 and thus also the cleaning element 501 with the annular carrier structure 502 is introduced into the patient receiving area 13, the annular carrier structure 502 can be pushed together by a funnel-shaped aspect of an introduction area of the patient receiving area 13 during its introduction into the patient receiving area 13. Through this the two ring elements 511, in particular with the end areas able to move in relation to one another, are moved toward each other and/or pushed inward, so that an overlap area between the two ring elements 511 is also enlarged. The effect of this is that the two ring elements 511 are put under tension and thus exert a force on the housing 27 surrounding the patient receiving area 13.

Moreover the cleaning element 501 has a cleaning covering 512 (FIGS. 10 to 13). The cleaning covering 501 comprises in the present exemplary aspect a textile fabric, in particular a non-woven material, and/or a foam. The cleaning covering 512, in particular the textile entity and/or the foam, is arranged here on a side pointing outward, in particular on a side facing toward the housing 27 surrounding the patient receiving area 13, of the annular carrier structure 502. For this purpose the annular carrier structure 502 also has on its outer side a receiving surface 513 for receiving the cleaning covering 512, in particular the textile entity and/or the foam. Preferably here the cleaning covering 512, in particular the textile entity and/or the foam, is removable here, for example arranged by a hook and loop connection on the receiving surface 513 of the annular carrier structure 502.

Through the arrangement of the cleaning covering 512, in particular of the textile entity and/or the foam, on the outer side of the annular carrier structure 502, the cleaning element 501 thus has a greater outer diameter than the inner diameter of the housing 27 surrounding the patient receiving area 13. The effect of this is that, after an introduction of the cleaning unit 500 into the patient receiving area 13, the cleaning element 501 rests with a force against the housing 27 surrounding the patient receiving area 13. Preferably the cleaning element 501 rests here with a force of 4 N to 6 N against the housing 27 surrounding the patient receiving area 13, so that a sufficiently great pressure for a mechanical cleaning is available, but a movement of the cleaning unit 500 through the patient receiving area 13 is also possible however.

Furthermore the cleaning unit 500 comprises two receiving elements 514 for receiving a cleaning agent (FIGS. 10 to 12). The two receiving elements 514 for receiving a cleaning agent are each arranged on an inner side 515 of a ring element 511 of the annular carrier structure 502. The receiving elements 514 can for example comprise a holder for receiving a commercially available cleaning agent container with cleaning agent and/or a commercially available disinfection agent container with disinfection agent.

Figure 13:
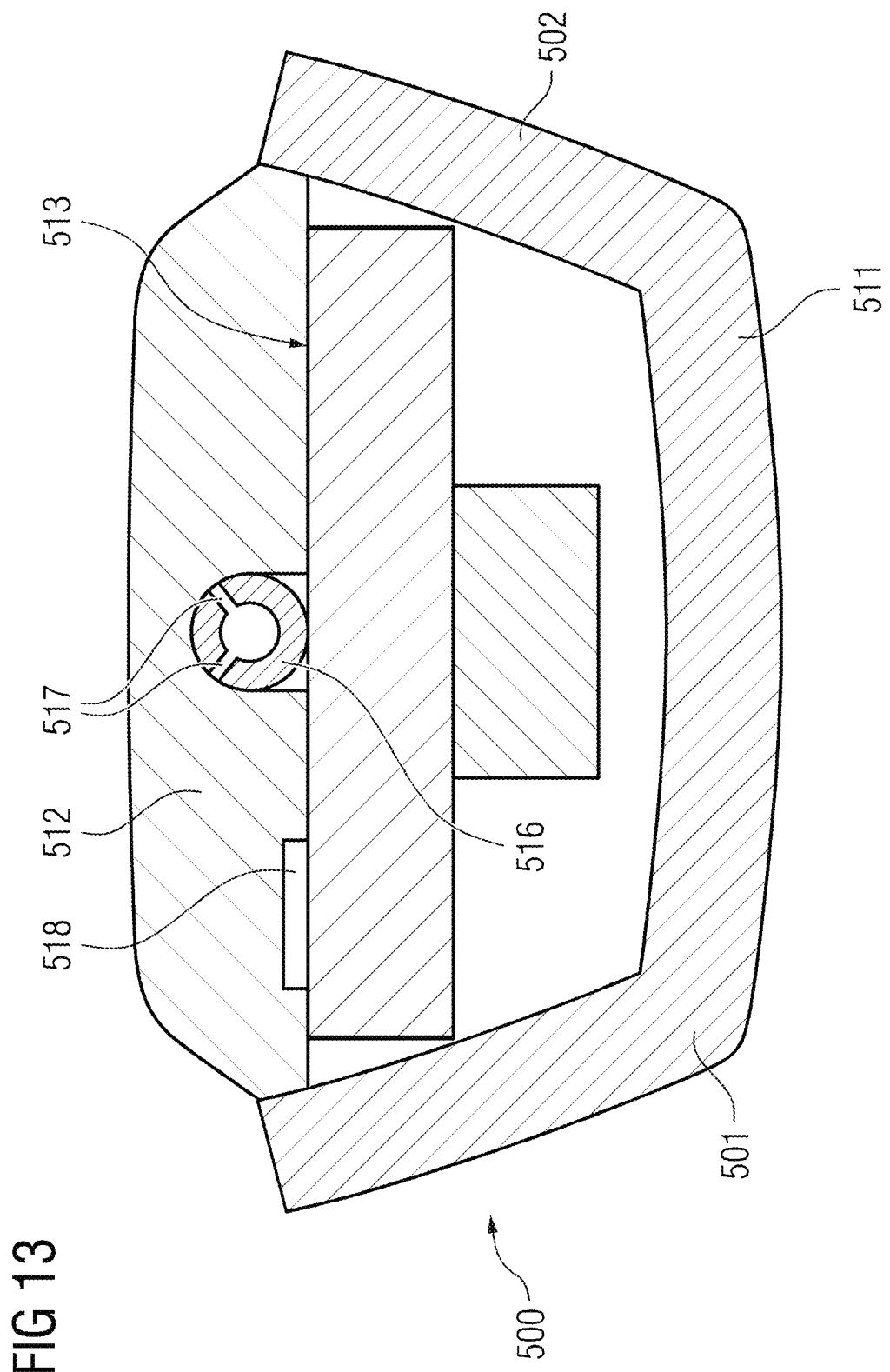
FIG. 13 shows the fifth exemplary aspect of the cleaning unit in a fourth view.

The cleaning element 501, in particular the annular carrier structure 502, has two cleaning agent channels 516, wherein one cleaning agent channel 516 is arranged in each case on one of the ring elements 511 of the annular carrier structure 502 (FIG. 13). The cleaning agent channels 516 are each arranged in a circumferential direction within the ring elements 511. In the present exemplary aspect the two cleaning agent channels 516 each comprise one cleaning agent hose. For a distribution of the cleaning agents the two cleaning agent channels 516 have openings 517, for example holes, on a side facing toward the cleaning covering 512. These openings 517 and/or holes are arranged at specific and/or defined distances on the cleaning agent channels 516. Also, for an even distribution of the cleaning agents, the opening 517 and/or holes can also have different sizes. For a distribution of the cleaning agent it is necessary in the present exemplary aspect for a user, in particular a medical operator, to press the cleaning agent container together and thus to convey the cleaning agent into the cleaning agent channels 516. Moreover it can also be conceivable for there to be an automatic control of the distribution of the cleaning agent.

Moreover, in the present exemplary aspect the cleaning element 501 has two sensors 518, which are embodied for detection of an amount of cleaning agent (FIG. 13). For this purpose the two sensors 518 are arranged on the receiving surface 513 of the annular carrier structure 502, in particular on one of the ring elements 511 in each case, and thus in direct contact with the cleaning agent surface 512. The detection and/or determination of the amount of cleaning agent are done here with the aid of a moisture value and/or a moisture content. For checking by a user the sensors 518 can also comprise an optical output means, such as an LED for example, which displays to the user whether the amount of cleaning agent is sufficient for a cleaning process. Moreover the two sensors 518 can also be connected to a control unit for automatic control of the cleaning agent distribution.

Furthermore the cleaning unit 500 can also have an electrical connection element, wherein an electrical connection element is not shown in any greater detail in FIGS. 10 to 13. An aspect and/or functioning of an electrical connection element correspond in this case to the description given for FIG. 6, to which the reader is herewith referred.

Figure 14:
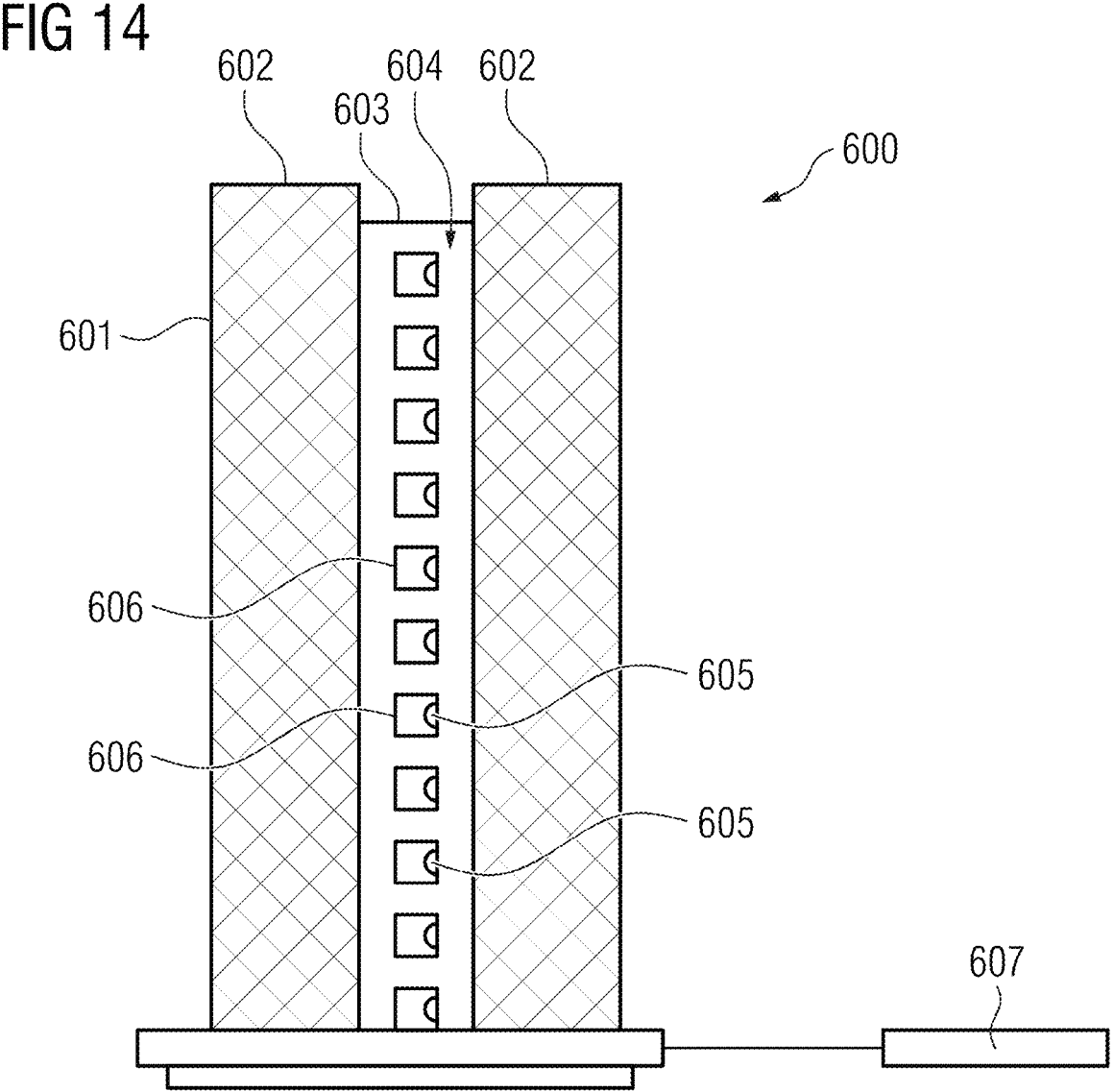
FIG. 14 shows a sixth exemplary aspect of the cleaning unit on the patient table of the medical imaging apparatus.

Shown in FIG. 14 is a sixth exemplary aspect of the cleaning unit 600. Components, features and functions that essentially remain the same are basically labeled with the same reference characters. The description given below essentially restricts itself to the differences from the exemplary aspect in FIGS. 10 to 13, wherein with regard to components, features and functions that essentially remain the same the reader is referred to the description of the exemplary aspect in FIGS. 10 to 13.

In FIG. 14 the cleaning unit is shown in a side view. The cleaning unit 600 in FIG. 14 differs from the cleaning unit 500 in FIGS. 10 to 13 by an alternate aspect of the cleaning covering 602. The cleaning unit 600 in the present exemplary aspect has two cleaning coverings 602, which are arranged at a distance from one another. To this end the cleaning unit 600, in particular an annular carrier structure 603 of the cleaning unit 600, has two contact surfaces, wherein a first contact surface is arranged in a front area and a second contact surface in a rear area of the annular carrier structure 603, in particular the side of the annular carrier structure 603 facing toward the housing 27 surrounding the patient receiving area 13. One aspect of the individual cleaning coverings 602 can correspond in this case to the information given for FIGS. 10 to 13, to which the reader is herewith referred.

Between the two cleaning coverings 602 the cleaning unit 600 has a receiving area 604 for receiving a plurality of UV-C illumination means 605 for a disinfection of the housing 27 surrounding the patient receiving area 13. In the present exemplary aspect the plurality of UV-C illumination means 605 are each formed by UV-C LEDs. The individual UV-C LEDs in this case are arranged in the annular carrier structure 603, in particular on an outer surface of the annular carrier structure 603. For this purpose the outer surface can also be embodied in the shape of a slot for a protected arrangement of the plurality of UV-C illumination means 605. The individual UV-C illumination means 605, in particular the UV-C LEDs, are arranged distributed in the circumferential direction on the outer side of the annular carrier structure 603.

The cleaning unit 600 furthermore has a plurality of light openings 606, which are arranged on an inner side of the annular carrier structure 603. Preferably the light openings 606 are arranged in the radial direction right through the annular carrier structure 603 so that a light from the illumination means, in particular the UV-C illumination means 605, can shine into the patient receiving area 13 and is thus visible for a patient and/or an observer.

Moreover it is also conceivable for the cleaning unit 600 to have light openings that are arranged on a side surface of the annular carrier structure 603. Moreover the cleaning unit 600 can comprise an illuminator that is embodied independently from a UV-C illuminator and is only provided for a visual representation of a cleaning process for a user and/or a patient.

The cleaning unit moreover has an electrical connection element 607. In this case the electrical connection element 607 is embodied identical in construction to a coil plug connector of a local radio frequency coil. An aspect and/or functioning of an electrical connection element 607 corresponds in this case to the description given for FIG. 6, to which the reader is herewith referred.

A further aspect of the cleaning unit 600 corresponds here to the cleaning unit described in FIGS. 10 to 13, to which the reader is herewith referred.

Although the disclosure has been illustrated and described in greater detail by the preferred exemplary aspect, the disclosure is not restricted by the disclosed examples and other variations can be derived herefrom by the person skilled in the art, without departing from the scope of protection of the disclosure.

The invention claimed is:

1. A cleaning unit for cleaning a housing of a medical imaging apparatus surrounding a patient receiving area, comprising at least one cleaning element, wherein the at least one cleaning element has an annular carrier structure, and a diameter of the cleaning element comprises at least one value of a diameter of the housing surrounding the patient receiving area, wherein the annular carrier structure has at least two ring elements with end areas movable relative to one another and configured to move inward and overlap when introduced into the patient receiving area, thereby creating tension to exert a cleaning force against an inner diameter of the housing surrounding the patient.

2. The cleaning unit as claimed in claim 1, wherein the at least one cleaning element has at least one base element configured to arrange the annular carrier structure within the patient receiving area.

3. The cleaning unit as claimed in claim 2, wherein the annular carrier structure has at least two ring elements, wherein the two ring elements are each arranged at a first end area on the at least one base element and with a second end area facing away from the at least one base element are arranged at least partly in a movable manner in relation to one another.

4. The cleaning unit as claimed in claim 1, wherein the at least one cleaning element has at least one cleaning covering, wherein the cleaning covering is arranged on the annular carrier structure.

5. The cleaning unit as claimed in claim 1, comprising at least one receiving element configured to receive a cleaning agent.

6. The cleaning unit as claimed in claim 5, wherein the at least one receiving element is arranged on an inner side of the annular carrier structure.

7. The cleaning unit as claimed in claim 1, wherein the at least one cleaning element has at least one cleaning agent channel, which is arranged at least partly running around within the annular carrier structure.

8. The cleaning unit as claimed in claim 1, wherein the at least one cleaning element has a sensor configured to detect an amount of cleaning agent.

9. The cleaning unit as claimed in claim 1, wherein the at least one cleaning element has a plurality of UV-C illuminators, which are arranged on an outer surface of the annular carrier structure.

10. The cleaning unit as claimed in claim 1, wherein the at least one cleaning element has at least one illuminator and at least one light opening, wherein the light opening is arranged on an inner side and/or a side surface of the annular carrier structure.

11. The cleaning unit as claimed in claim 1, further comprising an electrical connection element.

12. The cleaning unit as claimed in claim 11, wherein the electrical connection element is compatible with a plug socket of a patient table for an electrical contacting of local radio frequency coils.

13. A medical imaging apparatus comprising a scanner unit, a patient receiving area at least partly surrounded by the scanner unit, a housing surrounding the patient receiving area and a cleaning unit as claimed in claim 1.

14. The medical imaging apparatus as claimed in claim 13, wherein the annular carrier structure is arranged within the patient receiving area to clean the housing surrounding the patient receiving area and rests with a force against the housing surrounding the patient receiving area.

15. The medical imaging apparatus as claimed in claim 13, further comprising a patient support apparatus having a patient table movable within the patient receiving area, wherein the patient table has a receiving unit for an arrangement of the cleaning unit, and the receiving unit is arranged at a head end of the patient table.

16. The medical imaging apparatus as claimed in claim 15, wherein the patient table has an attachment rail for an attachment of at least one accessory unit, the receiving unit comprises the attachment rail, and the cleaning unit comprises at least one attachment element corresponding to the attachment rail.

17. The medical imaging apparatus as claimed in claim 15, wherein the cleaning unit has at least one attachment element and the receiving unit has at least one attachment element corresponding to the at least one attachment element of the cleaning unit on an end face side of the patient table.

18. The medical imaging apparatus as claimed in claim 17, wherein an attachment mechanism is arranged between the cleaning unit and the patient table in such a way that, when the patient table leaves the patient receiving area, the attachment mechanism is released.

19. The medical imaging apparatus as claimed in claim 15, wherein the cleaning unit has at least one attachment element and the receiving unit has at least one attachment element corresponding to the at least one attachment element of the cleaning unit, and the at least two attachment elements are configured such that, with a vertical movement of the patient table they connect or disconnect an attachment mechanism.

20. The medical imaging apparatus as claimed in claim 13, further comprising a patient support apparatus with a patient table and a rail system arranged within the patient receiving area for a guidance of the patient table within the patient receiving area, wherein the cleaning unit is arrangeable on the rail for cleaning the housing surrounding the patient receiving area.

* * * * *